(12) United States Patent
Palsson et al.

(10) Patent No.: US 7,788,041 B2
(45) Date of Patent: Aug. 31, 2010

(54) COMPOSITIONS AND METHODS FOR MODELING HUMAN METABOLISM

(75) Inventors: Bernard O. Palsson, San Diego, CA (US); Natalie Duarte, Scottsdale, AZ (US); Scott Becker, San Diego, CA (US); Neema Jamshidi, La Jolla, CA (US)

(73) Assignee: The Regents of the University of California, Oakland, CA (US)

( * ) Notice: Subject to any disclaimer, the term of this patent is extended or adjusted under 35 U.S.C. 154(b) by 0 days.

(21) Appl. No.: 11/866,945

(22) Filed: Oct. 3, 2007

(65) Prior Publication Data

US 2008/0133196 A1   Jun. 5, 2008

Related U.S. Application Data

(60) Provisional application No. 60/849,627, filed on Oct. 4, 2006.

(51) Int. Cl.
G06F 19/00 (2006.01)
G06F 7/00 (2006.01)

(52) U.S. Cl. .......................................... 702/19; 707/6
(58) Field of Classification Search ........................ None
See application file for complete search history.

(56) References Cited

U.S. PATENT DOCUMENTS

2004/0029149 A1   2/2004   Palsson et al.
2006/0147899 A1   7/2006   Famili et al.

FOREIGN PATENT DOCUMENTS

WO    WO 02/070730   *   9/2002

OTHER PUBLICATIONS

Duarte et al., "Global reconstruction of the human metabolic network based on genomic and bibliomic data", *PNAS*, 104(6):1777-1782 (2007).
Duarte et al., "Reconstruction and Validation of *Saccharomyces cerevisiae* iND750, a Fully Compartmentalized Genome-Scale Metabolic Model", *Genome Res.*, 14:1298-1309 (2004).
Förster et al., "Genome-Scale Reconstruction of the *Saccharomyces cerevisiae* Metabolic Network", *Genome Res.*, 13:244-253 (2003).
Kell, D.B., "The Virtual Human: Towards a Global Systems Biology of Multiscale, Distributed Biochemical Network Models", *IUBMB Life*, 59:689-695 (2007).
Lee et al., "Flux balance analysis in the era of metabolomics", *Briefings in Bioinformatics*, 7(2):140-150 (2006).
Mo et al., "A genome-scale, constraint-based approach to systems biology of human metabolism", *Molecular BioSystems*, 3:598-603 (2007).

* cited by examiner

*Primary Examiner*—Lori A Clow
(74) *Attorney, Agent, or Firm*—DLA Piper LLP (US)

(57) ABSTRACT

The present invention provides *Homo sapiens* Recon 1, a manually assembled, functionally validated, bottom-up reconstruction of human metabolism. Recon 1's 1496 genes, 2004 proteins, 2766 metabolites, and 3311 biochemical and transport reactions were extracted from more than 50 years of legacy biochemical knowledge and Build 35 of the human genome sequence.

25 Claims, 1 Drawing Sheet

COMPOSITIONS AND METHODS FOR MODELING HUMAN METABOLISM

CROSS REFERENCE TO RELATED APPLICATION(S)

This application claims the benefit of priority under 35 U.S.C. §119(e) of U.S. Ser. No. 60/849,627, filed Oct. 4, 2006, the entire contents of which are incorporated herein by reference.

BACKGROUND OF THE INVENTION

1. Field of the Invention

This invention relates generally to analysis of the activity of chemical reaction networks and, more specifically, to computational methods for simulating and predicting the activity of *Homo sapiens* (Human) reaction networks.

2. Background Information

Metabolism is vital to organism function and survival, and it is connected to essentially all aspects of cellular function in both physiological and patho-physiological states. Therefore, it is not surprising that metabolism is a key contributor to several important human diseases, including diabetes, obesity, cardiovascular disease, and cancer. Since metabolism has been carefully studied for decades in a variety of organisms, there is a collective knowledge base available that includes a legacy of valuable data, including many mechanistic reactions and well-characterized interactions. The procedure for integrating these data into a network reconstruction and predictive model has been well established for microorganisms and has recently been extended to mouse cellular metabolism (Sheikh, K., Forster, J. & Nielsen, L. K. Modeling hybridoma cell metabolism using a generic genome-scale metabolic model of *Mus musculus*. *Biolechnol Prog* 21, 112-21 (2005); Reed, J. L., Famili, I., Thiele, I. & Palsson, B. O. Towards multidimensional genome annotation. *Nat Rev Genet* 7, 130-41 (2006)).

It has been shown that even relatively minor changes in media composition can affect hundreds of components of these networks such that potentially hundreds of variables are worthy of consideration in making a prediction of cellular behavior. Similarly, due to the complexity of interactions in these networks, mutation of even a single gene can have effects on multiple components of the networks.

Thus, there exists a need for a model that describes Human reaction networks, such as the human metabolic network, which can be used to simulate many different aspects of cellular behavior under different conditions. The present invention satisfies this need, and provides related advantages as well. As such, the wealth of detailed biochemical information available for humans, combined with the recent sequencing and annotation of the human genome sequence (Finishing the euchromatic sequence of the human genome. *Nature* 431, 931-45 (2004)), has enabled the first comprehensive, bottom-up reconstruction of the global human metabolic network.

SUMMARY OF THE INVENTION

The invention provides a computer readable medium, which includes a data structure relating a plurality of *H. sapiens* reactants to a plurality of *H. sapiens* reactions, wherein each of the *H. sapiens* reactions includes one or more reactants identified as a substrate of the reaction, one or more reactants identified as a product of the reaction and a stoichiometric coefficient relating the substrate and the product, a constraint set for the plurality of *H. sapiens* reactions, and commands for determining at least one flux distribution that minimizes or maximizes an objective function when the constraint set is applied to the data representation, wherein at least one flux distribution is predictive of a *H. sapiens* physiological function. In one embodiment, the data structure comprises Tables 1, 4, 5, 7 and 8. In another embodiment, at least one of the cellular reactions in the data structure is annotated to indicate an associated gene listed in Table 3, and the computer readable medium further includes a gene database, as provided in Table 3, including information characterizing the associated gene. In another embodiment, at least one of the cellular reactions in the data structure is annotated with an assignment of function within one or more subsystems or compartments within the cell.

The invention also provides a method for predicting *H. sapiens* physiological function. The method includes providing a data structure relating a plurality of *H. sapiens* reactants to a plurality of *H. sapiens* reactions, wherein each of the *H. sapiens* reactions includes one or more reactants identified as a substrate of the reaction, one or more reactants identified as a product of the reaction and a stoichiometric coefficient relating the substrate and the product. The method further includes providing a constraint set for the plurality of *H. sapiens* reactions, providing an objective function, and determining at least one flux distribution that minimizes or maximizes the objective function when the constraint set is applied to the data structure, thereby predicting a *H. sapiens* physiological function. In one embodiment, the data structure comprises Tables 1, 4, 5, 7 and 8. In another embodiment, at least one of the *H. sapiens* reactions in the data structure is annotated to indicate an associated gene in Table 3, and the method predicts a *H. sapiens* physiological function related to the gene.

Also provided by the invention is a method for making a data structure relating a plurality of *H. sapiens* reactants to a plurality of *H. sapiens* reactions in a computer readable medium. The method includes identifying a plurality of *H. sapiens* reactions and a plurality of reactants that are substrates and products of the reactions, and relating the plurality of reactants to the plurality of reactions in a data structure, wherein each of the reactions includes one or more reactants identified as a substrate of the reaction, one or more reactants identified as a product of the reaction and a stoichiometric coefficient relating the substrate and the product. The method further includes determining a constraint set for the plurality of *H. sapiens* reactions, providing an objective function, determining at least one flux distribution that minimizes or maximizes the objective function when the constraint set is applied to the data structure, and (i) if at least one flux distribution is not predictive of a *H. sapiens* physiological function, then adding a reaction to or deleting a reaction from the data structure and repeating the previous step, or (ii) if at least one flux distribution is predictive of a *H. sapiens* physiological function, then storing the data structure in a computer readable medium. The invention further provides a data structure relating a plurality of *H. sapiens* reactants to a plurality of reactions, wherein the data structure is produced by the method.

DETAILED DESCRIPTION OF THE INVENTION

Figure 1:
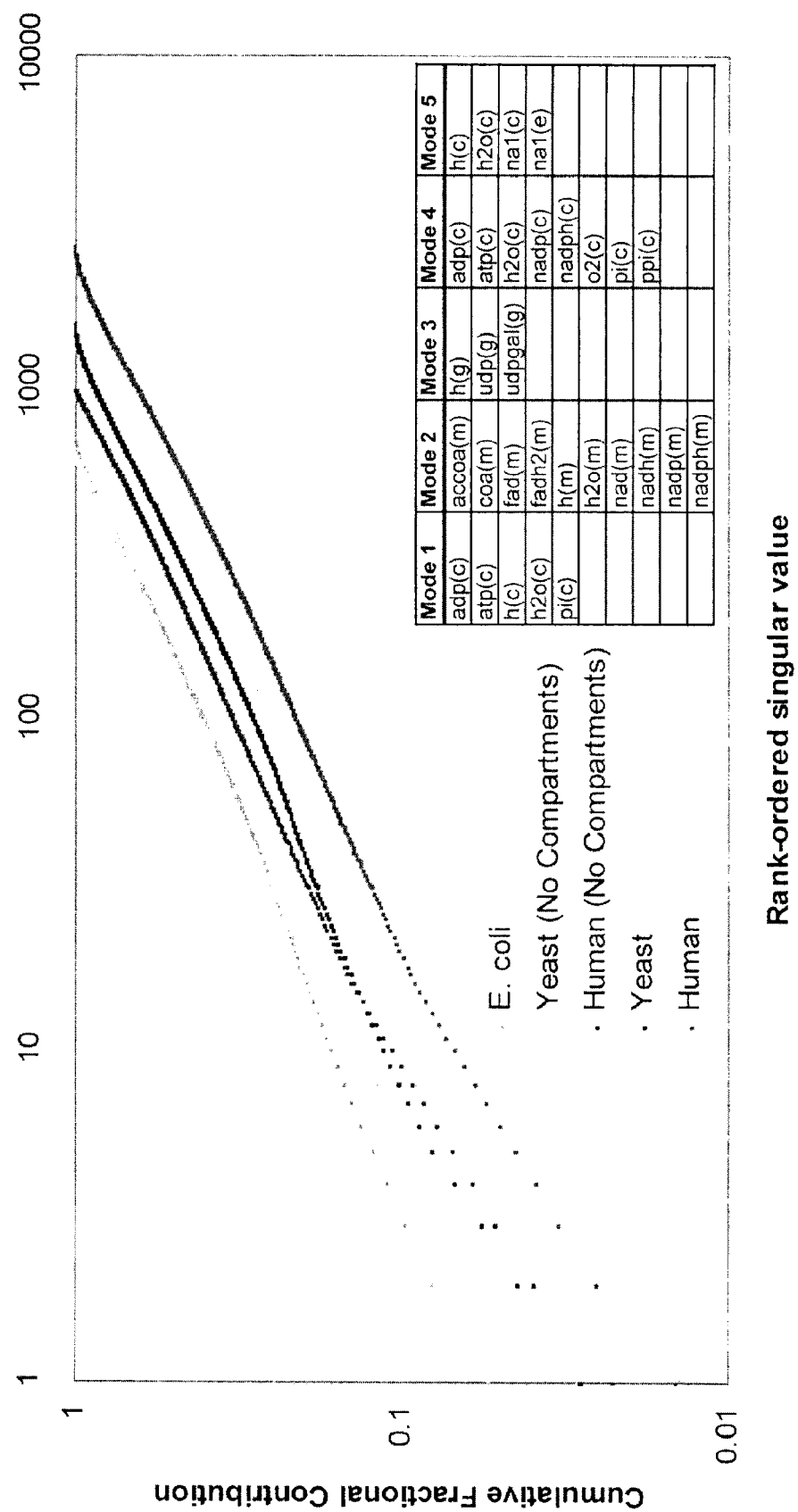
FIG. 1 is a graphical diagram showing normalized cumulative singular value spectra for *Homo sapiens*, *Saccharomyces cerevisiae*, and *Escherichia coli* and dominant metabolite modes. (A) Compartmentalized networks have a greater effective dimensionality than their non-compartmentalized counterparts, requiring a larger number of singular values to completely reconstruct the network. (B) The first five modes of the human metabolite coupling matrix highlight the importance of the production and exchange of energy equivalents and the potentially significant impact of osmotic regulation. Compartmental abbreviations: (c)—cytosolic, (e)—extracellular, (g)—Golgi apparatus, (m)—mitochondrial.

The present invention provides in silico models of human metabolic networks. The model can be used to simulate different aspects of cellular behavior of human cells under different environmental and genetic conditions, thereby providing valuable information for industrial and research applications. The models and methods can also be extended to simulate the activity of multiple interacting cells, including organs, physiological systems and whole body metabolism.

The human metabolic model can also be used to predict or validate the assignment of particular biochemical reactions to the enzyme-encoding genes found in the genome, and to identify the presence of reactions or pathways not indicated by current genomic data. Thus, the model can be used to guide the research and discovery process, potentially leading to the identification of new enzymes, medicines or metabolites of commercial importance.

As an example, the *Homo sapiens* metabolic models of the invention can be used to determine the effects of changes from aerobic to anaerobic conditions, such as occurs in skeletal muscles during exercise or in tumors, or to determine the effect of various dietary changes. The *Homo sapiens* metabolic models can also be used to determine the consequences of genetic defects, such as deficiencies in metabolic enzymes such as phosphofructokinase, phosphoglycerate kinase, phosphoglycerate mutase, lactate dehydrogenase and adenosine deaminase.

The *Homo sapiens* metabolic models can also be used to choose appropriate targets for drug design. Such targets include genes, proteins or reactants, which when modulated positively or negatively in a simulation produce a desired therapeutic result. The models and methods of the invention can also be used to predict the effects of a therapeutic agent or dietary supplement on a cellular function of interest. Likewise, the models and methods can be used to predict both desirable and undesirable side effects of the therapeutic agent on an interrelated cellular function in the target cell, as well as the desirable and undesirable effects that may occur in other cell types. Thus, the models and methods of the invention can make the drug development process more rapid and cost effective than is currently possible.

Cellular biochemical networks are analogous to chromosomes and are described in terms of reactions. Contigs are delineated by sequence reads, which describe individual base pairs, the primary components of a sequence annotation. Similarly, reactions are catalyzed by enzymes, which are derived from genes and their transcripts, and act on compounds, the primary components in a network annotation. The scope of genome annotation is clearly defined and has been significantly characterized, whereas biochemical networks vary across cell types and states and as a whole are largely uncharacterized.

The recent annotation of the human genome and growing availability of high-throughput data sets hold the promise of elucidating human physiology and disease at the cellular level through the reconstruction of biochemical reaction networks and the computational interrogation of their characteristics. Network reconstruction can be accomplished with a top-down or a bottom-up approach. The former infers network structure from large-scale data sets while the latter is based on direct evidence of component interactions. Bottom-up reconstruction leads to a biochemically, genetically and genomically structured (BiGG) database that can be used to compute allowable networks states under chemical and genetic constraints.

A well-annotated genome sequence enables the rapid identification of candidate network components (Reed, J. L., Famili, I., Thiele, I. & Palsson, B. O. Towards multidimensional genome annotation. *Nat Rev Genet* 7, 130-41 (2006)), and the assembly of a preliminary network (Romero, P. et al. Computational prediction of human metabolic pathways from the complete human genome. *Genome Biol* 6, R2 (2005)) that can be used as a starting point for manual curation. Enzyme Commission numbers (Nomenclature Committee of the International Union of Biochemistry and Molecular Biology. *Enzyme nomenclature* 1992. *IUB—recommendations of the Nomenclature Committee of the International Union of Biochemistry and Molecular Biology on the nomenclature and classification of enzymes* (ed. Webb, E. C.) (Academic Press, San Diego, 1992)) and Gene Ontologies (Ashburner, M. et al. Gene ontology: tool for the unification of biology. The Gene Ontology Consortium. *Nat Genet* 25, 25-9 (2000)) were used to identify an initial set of 1,865 human metabolic genes from the November 2004 annotations of Kyoto Encyclopedia of Genes and Genomes (KEGG) (Kanehisa, M. et al. From genomics to chemical genomics: new developments in KEGG. *Nucleic Acids Res* 34, D354-7 (2006)), NCBI's LocusLink (Pruitt, K. D. & Maglott, D. R. RefSeq and LocusLink: NCBI gene-centered resources. *Nucleic Acids Res* 29, 137-40 (2001)) (now EntrezGene (Pruitt, K. D. & Maglott, D. R. RefSeq and LocusLink: NCBI gene-centered resources. *Nucleic Acids Res* 29, 137-40 (2001)), and H-Invitational Database (Imanishi, T. et al. Integrative annotation of 21,037 human genes validated by full-length cDNA clones. *PLoS Biol* 2, e162 (2004)). These genes were mapped to a rudimentary network of 3,623 metabolic enzymes and 3,673 reactions from KEGG's LIGAND database and the compartmentalized yeast metabolic reconstruction (Duarte, N. C., Herrgard, M. J. & Palsson, B. O. Reconstruction and validation of *Saccharomyces cerevisiae* iND750, a fully compartmentalized genome-scale metabolic model. *Genome Res* 14, 1298-309 (2004)). In addition to establishing initial network scope, LIGAND's pathway-based organizational structure also facilitated parallel network assembly. Using strict quality control/quality assurance (QC/QA) standards, a team of researchers simultaneously curated network components by collecting biological evidence from over 1500 primary literature articles, reviews, and biochemical textbooks. By manually compiling data from literature sources we ensured that the network components and their interactions are based on direct physical evidence and reflect the current knowledge of human metabolism.

Thus, the models of the invention are based on a data structure relating a plurality of *H. sapiens* reactants to a plurality of *H. sapiens* reactions, wherein each of the *H. sapiens* reactions includes one or more reactants identified as a substrate of the reaction, one or more reactants identified as a product of the reaction and a stoichiometric coefficient relating the substrate and the product. The reactions included in the data structure can be those that are common to all or most *H. sapiens* cells, such as core metabolic reactions, or reactions specific for one or more given cell type.

Bottom-up reconstructions can be represented mathematically, enabling the computational interrogation of their properties. The basic functionality of the human metabolic network was thus validated by simulating 288 known metabolic functions in silico (see Tables 6-8). Initial component lists were derived from the genome annotation and pathway databases. Manual curation was then required for iterative rounds of reconstruction and gap analysis to form a functional, predictive model. Like genome sequence assembly and annotation, network reconstruction is an iterative process, and consequently several rounds of iterative gap analysis (i.e., targeted literature searches to find metabolic reactions that were missed initially) and comprehensive revalidation with strict QC/QA procedures were required to achieve a BiGG, high quality network. The result is *Homo sapiens* Recon 1, the largest functionally-validated reconstruction of a multi-cellular eukaryote to date (Tables 1-8).

TABLE 9

*Homo sapiens* Recon 1 network statistics.

| | |
|---|---:|
| Genes | 1,496 |
| Transcripts | 1,905 |
| Proteins | 2,004 |
| Complex-associated reactions | 248 |
| Isozyme-associated reactions | 946 |
| Intrasystem Reactions | 3,311 |
| Metabolic | 2,233 |
| Transport | 1,078 |
| Exchange Reactions | 432 |
| Metabolites | 2,712 |
| Cytosolic | 995 |
| Extracellular | 404 |
| Mitochondrial | 393 |
| Golgi Apparatus | 284 |
| Endoplasmic reticular | 235 |
| Lysosomal | 217 |
| Peroxisomal | 143 |
| Nuclear | 95 |
| Citations | 1,587 |
| Primary literature | 1,378 |
| Review articles | 188 |
| Textbooks | 21 |
| Validated metabolic functions | 288 |
| Knowledge gaps | 356 |

*Homo sapiens* Recon 1 was almost entirely constructed from human-specific data and includes many reactions directly extracted from the literature that are not described in any chart or database. It also is the most comprehensive eukaryotic reconstruction, with several hierarchical levels of detail, namely:

carefully formulated reactions which account for known reaction stoichiometry, substrate/cofactor specificity, and reversibility and are elementally and charge-balanced based on metabolite structure and formula at pH 7.2.

full compartmentalization of metabolites in and their exchange between seven intracellular locations (e.g., cytosol, mitochondria, nucleus, endoplasmic reticulum, Golgi apparatus, lysosome, peroxisome) and the extracellular environment.

precise Boolean descriptions of gene-protein relationships such as alternatively spliced variants, protein complexes, and isozymes.

confidence scores and literature references based on known biological evidence are associated with each reaction.

Various biological molecules, including but not limited to di- and triacylglycerol, sphingolipids, glycolipids, gangliosides, globosides, and cardiolipin involve the covalent incorporation of one or more fatty acid chains. Due to the large variety of different free fatty acids, there are a prohibitively large number of potential combinations of different lipids that can be incorporated into a particular class of compounds. For example, synthesis of diacylglycerol involves the incorporation of two fatty acids. This can be two C16, or a C16:1 in position 2 and a C18:2 in position 3, or any other combination of fatty acids. The combinatorial problem of dealing with these variations in composition for microorganisms have used 'averages' for defining a single type of each class of compound, i.e. an 'average' single diacylglycerol molecule. Since human tissues have significant variations in these compounds across the organ, tissues, and cell levels, not to mention differences between primary and cultured cells, a comprehensive, generalizing template framework needed to be developed in order to enable the incorporation and synthesis of a variety of compounds, without facing the combinatorial problems.

Different cells and tissues in humans have different populations for these compounds. As such, an "R-group formulation" was developed to meet these needs. This formulation enables the incorporation of any combination of fatty acids into the fatty acid containing metabolites, in a mass and charge balanced manner. Not all combinations are included at the same time and specific constraints need to be applied in order to produce a particular acylglycerol, sphingolipid, etc. This scheme has been enabled by defining a series of reactions that incorporate each fatty acid into "R-groups." There are three such R-groups in Recon 1 (R1, R2, and R3), each R-group synthesis reaction is 'scaled' to saturated 16 carbon fatty acid, thus each reaction converting a particular fatty acid into an R-group involves the appropriate cofactor exchange (nadph/nadp or fadh2/fad) and stoichiometry in order to balance the atomic elements.

Tailoring R-groups for a specific cell involves allowing only the appropriate R-group synthesis reactions to be open, and closing the constraints for all of the fatty acids that are not to be included.

Accordingly, the entire contents of Homo sapiens Recon 1 is stored in several formats (searchable database, metabolite and reaction lists, human-specific metabolic maps, stoichiometric matrix, Systems Biology Markup Language (The Math Works, Inc.)) on a password protected internal website at bigg.ucsd.edu and in Tables 1-8.

Recon 1 summarizes current knowledge of the human metabolic network in a structured, mathematical format that enables systematic studies of human metabolism and its properties. It has many potential research applications, including the global assessment of network confidence and identification of gaps in our knowledge base, the study of network properties of the human metabolic map, and the simultaneous analysis of transcriptomic, proteomic, and fluxomic data in the context of known biochemical interactions or pathways.

For example, Recon 1 provides *H. sapiens* metabolic networks that include, but are not limited to amino acid metabolism, carbohydrate metabolism, energy metabolism, glycan metabolism, lipid metabolism, nucleotide metabolism, secondary metabolism (e.g., xenobiotic metabolism), vitamin metabolism and cofactor metabolism. As such, exemplary metabolic pathways include, but are not limited to: Glycine, serine and threonine metabolism; Collagen degradation; Methionine and cysteine metabolism; Urea cycle/Arg and Pro metabolism; Valine, Leucine, Isoleucine degradation; Galactose metabolism; Ascorbate metabolism; Fructose, mannose, fucose metabolism; Glycogen biosynthesis; Glycogen degradation; Starch degradation; Di- and polysaccharide degradation; Aminosugars metabolism; Glyoxylate metabolism; Glycolysis; Methylglyoxal metabolism; Pentose and glucuronate interconversions; Nucleotide sugar metabolism; TCA cycle; Inositol phosphate metabolism; Itaconate and mesaconate metabolism; Propanoate metabolism; Butanoate metabolism; Oxidative phosphorylation and ROS detoxification; Keratan sulfate biosynthesis; Hyaluronan metabolism; Chondroitin sulfate biosynthesis; Dolichol Biosynthesis; GPI anchor biosynthesis; O-Glycan biosynthesis; N-Glycan Biosynthesis; N-Glycan degradation; Glycerophospholipid metabolism; Bile Acid biosynthesis; Glood Group biosynthesis; Cholesterol metabolism; Elcosanoid metabolism; Carnitine shuttle; Sphingolipid metabolism; Globoside metabolism; Ganglioside metabolism; Steroid metabolism; Fatty Acid metabolism; R-Group synthesis; Triacylglycerol metabolism; IMP synthesis; Purine metabolism; Purine catabolism; UMP Synthesis; Pyrimidine catabolism; Deoxynucleotides synthesis; Trepenoid biosynthesis; Limonene and pinene degradation; Alkaloid biosynthesis; Indol and ipecac alkaloid biosynthesis; Stilbene, coumarine and lignin biosynthesis; Novobiocin biosynthesis; Streptomycin biosynthesis; Tetracycline biosynthesis; Vitamin K, B6, A D metabolism; Thiamine metabolism; CoA biosynthesis; CoA catabolism; Folate metabolism; Ubiquinon 10 biosynthesis; Biotin metabolism; Folate metabolism; NAD metabolism; Heme biosynthesis; Heme degradation; Riboflavin metabolism; and Tetrahydrobiopterin metabolism.

As used herein, the terms "*H. sapiens* reaction" and "*Homo sapiens* reaction" are intended to mean a conversion that consumes a substrate or forms a product that occurs in the human metabolic network. The term can include a conversion that occurs due to the activity of one or more enzymes that are genetically encoded by the human genome. The term can also include a conversion that occurs spontaneously in a human cell. Conversions included in the term include, for example, changes in chemical composition such as those due to nucleophilic or electrophilic addition, nucleophilic or electrophilic substitution, elimination, isomerization, deamination, phosphorylation, methylation, glycolysation, reduction, oxidation or changes in location such as those that occur due to a transport reaction that moves one or more reactants within the same compartment or from one cellular compartment to another. In the case of a transport reaction, the substrate and product of the reaction can be chemically the same and the substrate and product can be differentiated according to location in a particular cellular compartment. Thus, a reaction that transports a chemically unchanged reactant from a first compartment to a second compartment has as its substrate the reactant in the first compartment and as its product the reactant in the second compartment. It will be understood that when used in reference to an in silico model or data structure, a reaction is intended to be a representation of a chemical conversion that consumes a substrate or produces a product.

As used herein, the terms "*H. sapiens* reactant" and "*Homo sapiens* reactant" are intended to mean a chemical that is a substrate or a product of a reaction that occurs in the human metabolic network. The term can include substrates or products of reactions performed by one or more enzymes encoded by human gene(s), reactions occurring in human cells that are performed by one or more non-genetically encoded macromolecule, protein or enzyme, or reactions that occur spontaneously in a human cell. Metabolites are understood to be reactants within the meaning of the term. It will be understood that when used in reference to an in silico model or data structure, a reactant is intended to be a representation of a chemical that is a substrate or a product of a reaction that occurs in a human cell.

As used herein the term "substrate" is intended to mean a reactant that can be converted to one or more products by a reaction. The term can include, for example, a reactant that is to be chemically changed due to nucleophilic or electrophilic addition, nucleophilic or electrophilic substitution, elimination, isomerization, deamination, phosphorylation, methylation, reduction, oxidation or that is to change location such as by being transported across a membrane or to a different compartment.

As used herein, the term "product" is intended to mean a reactant that results from a reaction with one or more substrates. The term can include, for example, a reactant that has been chemically changed due to nucleophilic or electrophilic addition, nucleophilic or electrophilic substitution, elimination, isomerization, deamination, phosphorylation, methylation, reduction or oxidation or that has changed location such as by being transported across a membrane or to a different compartment.

As used herein, the term "stoichiometric coefficient" is intended to mean a numerical constant correlating the number of one or more reactants and the number of one or more products in a chemical reaction. Typically, the numbers are integers as they denote the number of molecules of each reactant in an elementally balanced chemical equation that describes the corresponding conversion. However, in some cases the numbers can take on non-integer values, for example, when used in a lumped reaction or to reflect empirical data.

As used herein, the term "plurality," when used in reference to *H. sapiens* reactions or reactants is intended to mean at least 2 reactions or reactants. The term can include any number of *H. sapiens* reactions or reactants in the range from 2 to the number of naturally occurring reactants or reactions for a particular human cell. Thus, the term can include, for example, at least 10, 20, 30, 50, 100, 150, 200, 300, 400, 500, 600 or more reactions or reactants. The number of reactions or reactants can be expressed as a portion of the total number of naturally occurring reactions for a particular human cell such as at least 20%, 30%, 50%, 60%, 75%, 90%, 95% or 98% of the total number of naturally occurring reactions that occur in the particular human cell.

As used herein, the term "data structure" is intended to mean a physical or logical relationship among data elements, designed to support specific data manipulation functions. The term can include, for example, a list of data elements that can be added combined or otherwise manipulated such as a list of representations for reactions from which reactants can be related in a matrix or network. The term can also include a matrix that correlates data elements from two or more lists of information such as a matrix that correlates reactants to reactions. Information included in the term can represent, for example, a substrate or product of a chemical reaction, a chemical reaction relating one or more substrates to one or more products, a constraint placed on a reaction, or a stoichiometric coefficient.

As used herein, the term "constraint" is intended to mean an upper or lower boundary for a reaction. A boundary can specify a minimum or maximum flow of mass, electrons or energy through a reaction. A boundary can further specify directionality of a reaction. A boundary can be a constant value such as zero, infinity, or a numerical value such as an integer and non-integer. Alternatively, a boundary can be a variable boundary value as set forth below.

As used herein, the term "variable," when used in reference to a constraint is intended to mean capable of assuming any of a set of values in response to being acted upon by a constraint function. The term "function," when used in the context of a constraint, is intended to be consistent with the meaning of the term as it is understood in the computer and mathematical arts. A function can be binary such that changes correspond to a reaction being off or on. Alternatively, continuous functions can be used such that changes in boundary values correspond to increases or decreases in activity. Such increases or decreases can also be binned or effectively digitized by a function capable of converting sets of values to discreet integer values. A function included in the term can correlate a boundary value with the presence, absence or amount of a biochemical reaction network participant such as a reactant, reaction, enzyme or gene. A function included in the term can correlate a boundary value with an outcome of at least one reaction in a reaction network that includes the reaction that is constrained by the boundary limit. A function included in the term can also correlate a boundary value with an environmental condition such as time, pH, temperature or redox potential.

As used herein, the term "activity," when used in reference to a reaction, is intended to mean the amount of product produced by the reaction, the amount of substrate consumed by the reaction or the rate at which a product is produced or a substrate is consumed. The amount of product produced by the reaction, the amount of substrate consumed by the reaction or the rate at which a product is produced or a substrate is consumed can also be referred to as the flux for the reaction.

As used herein, the term "flux distribution" refers to a directional, quantitative list of values corresponding to the set of reactions in a network, representing the mass flow per unit time for each reaction.

As used herein, the term "constraint set" refers to the collection of constraints for every flux in a reaction network.

As used herein, the term "growth" refers to the production of a weighted sum of metabolites identified as biomass components.

As used herein, the term "energy production" refers to the production of metabolites that store energy in their chemical bonds, particularly high energy phosphate bonds such as ATP and GTP.

As used herein, the term "redox equivalent" refers to a metabolite that can alter the oxidation state of other metabolites, generally through the transfer of electrons and or protons.

As used herein, the term "biomass" refers to a set of metabolites that are required for cellular functions including replication, maintenance, and/or survival. As such, the term "biomass precursor" refers to a metabolite that can be converted to or is a member of the class of biomass metabolites.

As used herein, the term "bioactive small molecule" refers to a metabolite that can inhibit or activate another biological compound, including metabolites, proteins, and nucleic acid polymers.

As used herein, the term "cofactor" refers to a metabolite or chemical compound that is required for a catalytic activity of an enzyme to be carried out.

As used herein, the term "optimization problem" refers to a problem whose solution is obtained through the calculation of a minimum (or maximum) value of the objective function.

As used herein, the term "objective function" refers to a physiological function that can be described in terms of the data structure of Recon 1, generally in terms of one or more weighted sum or product of reactions.

As used herein, the term "R-group" refers to a fatty acid hydrocarbon chain.

The invention provides a computer readable medium, having a data structure relating a plurality of *H. sapiens* reactants to a plurality of *H. sapiens* reactions, wherein each of the *H. sapiens* reactions includes one or more reactants identified as a substrate of the reaction, one or more reactants identified as a product of the reaction and a stoichiometric coefficient relating the substrate and the product.

Depending on the application, the plurality of *H. sapiens* reactions can include reactions selected from core metabolic reactions or peripheral metabolic reactions. As used herein, the term "core," when used in reference to a metabolic pathway, is intended to mean a metabolic pathway selected from glycolysis/gluconeogenesis, the pentose phosphate pathway (PPP), the tricarboxylic acid (TCA) cycle, glycogen storage, electron transfer system (ETS), the malate/aspartate shuttle, the glycerol phosphate shuttle, and plasma and mitochondrial membrane transporters. As used herein, the term "peripheral," when used in reference to a metabolic pathway, is intended to mean a metabolic pathway that includes one or more reactions that are not a part of a core metabolic pathway. In one embodiment, the plurality of *H. sapiens* reactions are those that form Recon 1.

A plurality of *H. sapiens* reactants can be related to a plurality of *H. sapiens* reactions in any data structure that represents, for each reactant, the reactions by which it is consumed or produced. Thus, the data structure, which is referred to herein as a "reaction network data structure," serves as a representation of a biological reaction network or system. An example of a reaction network that can be represented in a reaction network data structure of the invention is the collection of reactions that constitute the metabolic reactions of a human cell (i.e., Recon 1).

The reactions to be included in a particular network data structure of *Homo sapiens* can be determined experimentally using, for example, gene or protein expression profiles, where the molecular characteristics of the cell can be correlated to the expression levels. The expression or lack of expression of genes or proteins in a cell type can be used in determining whether a reaction is included in the model by association to the expressed gene(s) and or protein(s). Thus, it is possible to use experimental technologies to determine which genes and/or proteins are expressed in a specific cell type, and to further use this information to determine which reactions are present in the cell type of interest. In this way a subset of reactions from all of those reactions that can occur in human cells are selected to comprise the set of reactions that represent a specific cell type. cDNA expression profiles have been demonstrated to be useful, for example, for classification of breast cancer cells (Sorlie et al., *Proc. Natl. Acad. Sci. U.S.A.* 98(19): 10869-10874 (2001)).

The methods and models of the invention can be applied to any *H. sapiens* cell type at any stage of differentiation, including, for example, embryonic stem cells, hematopoietic stem cells, differentiated hematopoietic cells, skeletal muscle cells, cardiac muscle cells, smooth muscle cells, skin cells, nerve cells, kidney cells, pulmonary cells, liver cells, adipocytes and endocrine cells (e.g., beta islet cells of the pancreas, mammary gland cells, adrenal cells, and other specialized hormone secreting cells).

The methods and models of the invention can be applied to normal cells or pathological cells. Normal cells that exhibit a variety of physiological activities of interest, including homeostasis, proliferation, differentiation, apoptosis, contraction and motility, can be modeled. Pathological cells can also be modeled, including cells that reflect genetic or developmental abnormalities, nutritional deficiencies, environmental assaults, infection (such as by bacteria, viral, protozoan or fungal agents), neoplasia, aging, altered immune or endocrine function, tissue damage, or any combination of these factors. The pathological cells can be representative of any type of human pathology, including, for example, various metabolic disorders of carbohydrate, lipid or protein metabolism, obesity, diabetes, cardiovascular disease, fibrosis, various cancers, kidney failure, immune pathologies, neurodegenerative diseases, and various monogenetic metabolic diseases described in the Online Mendelian Inheritance in Man database (Center for Medical Genetics, Johns Hopkins University (Baltimore, Md.) and National Center for Biotechnology Information, National Library of Medicine (Bethesda, Md.).

The methods and models of the invention can also be applied to cells undergoing therapeutic perturbations, such as cells treated with drugs that target participants in a reaction network, cells treated with gene-based therapeutics that increase or decrease expression of an encoded protein, and cells treated with radiation. As used herein, the term "drug" refers to a compound of any molecular nature with a known or proposed therapeutic function, including, for example, small molecule compounds, peptides and other macromolecules, peptidomimetics and antibodies, any of which can optionally be tagged with cytostatic, targeting or detectable moieties. The term "gene-based therapeutic" refers to nucleic acid therapeutics, including, for example, expressible genes with normal or altered protein activity, antisense compounds, ribozymes, DNAzymes, RNA interference compounds (RNAi) and the like. The therapeutics can target any reaction network participant, in any cellular location, including participants in extracellular, cell surface, cytoplasmic, mitochondrial and nuclear locations. Experimental data that are gathered on the response of cells to therapeutic treatment, such as alterations in gene or protein expression profiles, can be used to tailor a network for a pathological state of a particular cell type.

The methods and models of the invention can be applied to H. sapiens cells as they exist in any form, such as in primary cell isolates or in established cell lines, or in the whole body, in intact organs or in tissue explants. Accordingly, the methods and models can take into account intercellular communications and/or inter-organ communications, the effect of adhesion to a substrate or neighboring cells (such as a stem cell interacting with mesenchymal cells or a cancer cell interacting with its tissue microenvironment, or beta-islet cells without normal stroma), and other interactions relevant to multicellular systems.

The reactants to be used in a reaction network data structure of the invention can be obtained from or stored in a compound database. As used herein, the term "compound database" is intended to mean a computer readable medium containing a plurality of molecules that includes substrates and products of biological reactions. The plurality of molecules can include molecules found in multiple organisms, thereby constituting a universal compound database. Alternatively, the plurality of molecules can be limited to those that occur in a particular organism, thereby constituting an organism-specific compound database. Each reactant in a compound database can be identified according to the chemical species and the cellular compartment in which it is present. Thus, for example, a distinction can be made between glucose in the extracellular compartment versus glucose in the cytosol. Additionally each of the reactants can be specified as a metabolite of a primary or secondary metabolic pathway. Although identification of a reactant as a metabolite of a primary or secondary metabolic pathway does not indicate any chemical distinction between the reactants in a reaction, such a designation can assist in visual representations of large networks of reactions.

As used herein, the term "compartment" is intended to mean a subdivided region containing at least one reactant, such that the reactant is separated from at least one other reactant in a second region. A subdivided region included in the term can be correlated with a subdivided region of a cell. Thus, a subdivided region included in the term can be, for example, the intracellular space of a cell; the extracellular space around a cell; the periplasmic space; the interior space of an organelle such as a mitochondrium, endoplasmic reticulum, Golgi apparatus, vacuole or nucleus; or any subcellular space that is separated from another by a membrane or other physical barrier. Subdivided regions can also be made in order to create virtual boundaries in a reaction network that are not correlated with physical barriers. Virtual boundaries can be made for the purpose of segmenting the reactions in a network into different compartments or substructures.

As used herein, the term "substructure" is intended to mean a portion of the information in a data structure that is separated from other information in the data structure such that the portion of information can be separately manipulated or analyzed. The term can include portions subdivided according to a biological function including, for example, information relevant to a particular metabolic pathway such as an internal flux pathway, exchange flux pathway, central metabolic pathway, peripheral metabolic pathway, or secondary metabolic pathway. The term can include portions subdivided according to computational or mathematical principles that allow for a particular type of analysis or manipulation of the data structure.

The reactions included in a reaction network data structure can be obtained from a metabolic reaction database that includes the substrates, products, and stoichiometry of a plurality of human metabolic reactions. The reactants in a reaction network data structure can be designated as either substrates or products of a particular reaction, each with a stoichiometric coefficient assigned to it to describe the chemical conversion taking place in the reaction. Each reaction is also described as occurring in either a reversible or irreversible direction. Reversible reactions can either be represented as one reaction that operates in both the forward and reverse direction or be decomposed into two irreversible reactions, one corresponding to the forward reaction and the other corresponding to the backward reaction.

Reactions included in a reaction network data structure can include intra-system or exchange reactions. Intra-system reactions are the chemically and electrically balanced interconversions of chemical species and transport processes, which serve to replenish or drain the relative amounts of certain metabolites. These intra-system reactions can be classified as either being transformations or translocations. A transformation is a reaction that contains distinct sets of compounds as substrates and products, while a translocation contains reactants located in different compartments. Thus, a reaction that simply transports a metabolite from the extracellular environment to the cytosol, without changing its chemical composition is solely classified as a translocation, while a reaction such as the phosphotransferase system (PTS) which takes extracellular glucose and converts it into cytosolic glucose-6-phosphate is a translocation and a transformation.

Exchange reactions are those which constitute sources and sinks, allowing the passage of metabolites into and out of a compartment or across a hypothetical system boundary. These reactions are included in a model for simulation purposes and represent the metabolic demands placed on a human cell. While they may be chemically balanced in certain cases, they are typically not balanced and can often have only a single substrate or product. As a matter of convention the exchange reactions are further classified into demand exchange and input/output exchange reactions.

Input/output exchange reactions are used to allow extracellular reactants to enter or exit the reaction network represented by a model of the invention. For each of the extracellular metabolites a corresponding input/output exchange reaction can be created. These reactions can either be irreversible or reversible with the metabolite indicated as a substrate with a stoichiometric coefficient of one and no products produced by the reaction. This particular convention is adopted to allow the reaction to take on a positive flux value (activity level) when the metabolite is being produced or removed from the reaction network and a negative flux value when the metabolite is being consumed or introduced into the reaction network. These reactions will be further constrained during the course of a simulation to specify exactly which metabolites are available to the cell and which can be excreted by the cell.

A demand exchange reaction is always specified as an irreversible reaction containing at least one substrate. These reactions are typically formulated to represent the production of an intracellular metabolite by the metabolic network or the aggregate production of many reactants in balanced ratios such as in the representation of a reaction that leads to biomass formation, also referred to as growth.

A demand exchange reaction can be introduced for any metabolite in a model of the invention. Most commonly these reactions are introduced for metabolites that are required to be produced by the cell for the purposes of creating a new cell such as amino acids, nucleotides, phospholipids, and other biomass constituents, or metabolites that are to be produced for alternative purposes. Once these metabolites are identified, a demand exchange reaction that is irreversible and specifies the metabolite as a substrate with a stoichiometric coefficient of unity can be created. With these specifications, if the reaction is active it leads to the net production of the metabolite by the system meeting potential production demands. Examples of processes that can be represented as a demand exchange reaction in a reaction network data structure and analyzed by the methods of the invention include, for example, production or secretion of an individual protein; production or secretion of an individual metabolite such as an amino acid, vitamin, nucleoside, antibiotic or surfactant; production of ATP for extraneous energy requiring processes such as locomotion; or formation of biomass constituents.

In addition to these demand exchange reactions that are placed on individual metabolites, demand exchange reactions that utilize multiple metabolites in defined stoichiometric ratios can be introduced. These reactions are referred to as aggregate demand exchange reactions. An example of an aggregate demand reaction is a reaction used to simulate the concurrent growth demands or production requirements associated with cell growth that are placed on a cell, for example, by simulating the formation of multiple biomass constituents simultaneously at a particular cellular growth rate.

Accordingly, bottom-up reconstruction of Recon 1 required extensive, manual surveys of the primary literature to evaluate biological evidence associated with each gene, protein, and reaction. Viewing confidence scores in these individual components at the system level reveals a global knowledge landscape with specific "peaks" and "valleys" in the understanding of human metabolism. Four categories of metabolic pathways were identified based on the degree of characterization of their corresponding reactions. Chondroitin sulfate catabolism is a typical example of a Category I pathway in which nearly all of the enzymes have been biochemically characterized and their corresponding genes have been identified. Category II pathways, such as glyoxylate metabolism, have a roughly equal proportion of high confidence reactions and those with moderate biological evidence (see Example 1). For instance, the presence of glycerate kinase (GLYCK2) was inferred based on the observation that individuals with D-glycericaciduria (who lack this enzyme) cannot further metabolize D-glycerate and excrete gram amounts of it in their urine (Poore, R. E., Hurst, C. H., Assimos, D. G. & Holmes, R. P. Pathways of hepatic oxalate synthesis and their regulation. *Am J Physiol* 272, C289-94 (1997)). Category III pathways exhibit a wide range of confidence scores and gene coverage. The fact that some of these pathways have not been completely elucidated is surprising, and arguably these knowledge deficits may not have been identified without a systems approach. For example, the mechanism which cycles the end products of ascorbate degradation back to the glycolytic pathway appear to be poorly understood. Furthermore, while most of ubiquinone 10 biosynthesis was inferred from physiological evidence, there appears to be a few well-studied enzymes that are interspersed between these poorly characterized reactions. A large number of intracellular transport reactions are also included in this category, indicating that as a whole they require considerably more investigation. Thus, the reconstruction of *Homo sapiens* Recon 1 has resulted in a comprehensive review of our knowledge of human metabolism and has lead to direct suggestions where further experimental studies are needed (see Tables 1-5).

Recon 1 has also enabled in silico characterization of the known human metabolic map using well-established constraint-based methods that have been applied extensively to microbial cells (Trawick, J. D. & Schilling, C. H. Use of constraint-based modeling for the prediction and validation of antimicrobial targets. *Biochem Pharmacol* 71, 1026-35 (2006)). Flux coupling analysis (Burgard, A. P., Nikolaev, E. V., Schilling, C. H. & Maranas, C. D. Flux coupling analysis of genome-scale metabolic network reconstructions. *Genome Res* 14, 301-12 (2004)) was used to identify coupled reaction sets under aerobic glucose uptake conditions. Coupled reaction sets consist of reactions that are active together in integrated functional states of a network (Jamshidi, N. & Palsson, B. Systems Biology of SNPs: Correlated Reaction Sets and Phenotypes. (accepted for publication, MSB) (2006); Papin, J. A., Reed, J. L. & Palsson, B. O. Hierarchical thinking in network biology: the unbiased modularization of biochemical networks. *Trends Biochem Sci* 29, 641-7 (2004)). Perturbation of one reaction leads to perturbations in the others, since they are all coupled. One of the largest of the 250+ coupled reaction sets involves two branches of cholesterol biosynthesis. HMG-CoA reductase, the target of the antilipidemic class of statin drugs, is in this coupled reaction set. If this reaction-set persists under different input conditions, it could provide a means for identifying multiple drug targets for treating hyperlipidemia. It has been suggested that deficiencies in enzymes belonging to the same functionally coupled reaction set may have similar phenotypes and examples of this have been reported for the human mitochondria (Jamshidi, N. & Palsson, B. O. Systems Biology of SNPs. *Molecular Systems Biology* accepted (2006)).

The Mendelian Inheritance in Man (MIM) (Hamosh, A., Scott, A. F., Amberger, J. S., Bocchini, C. A. & McKusick, V. A. Online Mendelian Inheritance in Man (OMIM), a knowledgebase of human genes and genetic disorders. *Nucleic Acids Res* 33, D514-7 (2005)) identification tags associated with the genes encoding glutathione synthetase (GTHS; OMIM: #231900) and glutamate-cysteine ligase (GLUCYS; OMIM: #230450) indicate that both deficiencies result in hemolytic anemia. Reactions in the glutathione reaction set were mapped to disease associations using Mendelian Inheritance in Man identification tags. Deficiencies in glutathione synthetase (GTHS) or glutamate-cysteine ligase (GLUCYS) both result in hemolytic anemia, supporting the notion that enzyme deficiencies in the same coupled set may have similar phenotypes. These examples demonstrate that developing models from a reconstruction enables functional investigation, provides an analytical approach to studying the causes and consequences of disease states, and may potentially lead to insights into new drug treatment targets. The use of functionally grouped reactions, such as coupled reaction sets (Burgard, A. P., Nikolaev, E. V., Schilling, C. H. & Maranas, C. D. Flux coupling analysis of genome-scale metabolic network reconstructions. *Genome Res* 14, 301-12 (2004)) and correlated reaction sets (co-sets) (Thiele, I., Price, N. D., Vo, T. D. & Palsson, B. O. Candidate metabolic network states in human mitochondria. Impact of diabetes, ischemia, and diet. *J Biol Chem* 280, 11683-95 (2005)) present a promising approach for the functional analysis of complex networks with applications in elucidating causal relationships in the diseases and potentially identifying new treatment strategies (Papin, J. A., Reed, J. L. & Palsson, B. O. Hierarchical thinking in network biology: the unbiased modularization of biochemical networks. *Trends Biochem Sci* 29, 641-7 (2004)).

Network analysis was also used to identify Recon 1's systemic reactions and assess network dimensionality. Singular value decomposition (SVD) of Recon 1's stoichiometric matrix (S) (Famili, I. & Palsson, B. O. Systemic metabolic reactions are obtained by singular value decomposition of genome-scale stoichiometric matrices. *J Theor Biol* 224, 87-96 (2003)) and construction of its metabolite coupling matrix (M) (Becker, S. A., Price, N. D. & Palsson, B. O. Metabolite coupling in genome-scale metabolic networks. *BMC Bioinformatics* 7, 111 (2006)) revealed that compartmentalization has a noticeable effect on the systemic characteristics of human metabolism (FIG. 1). Compartmentalization significantly increases the effective dimensionality of a metabolic network, which can increase the functional capabilities of the network (Palsson, B. O. *Systems Biology: Determining the Capabilities of Reconstructed Networks* (Cambridge Univ Pr, 2006)). The five most dominant modes of the SVD of M (shown in FIG. 1 table inset), interpreted as independent groups of interacting metabolites, have biologically meaningful interpretations as currency exchanges including high energy phosphate group transfer, reducing equivalent exchange, and sugar transfer. Interestingly, these modes are compartment-specific, highlighting the relationship between intracellular compartmentalization and cellular functions. Collectively, these observations highlight some of the implications of compartmentalization in the human metabolic reconstruction and support the notion that compartments may function as independent reaction sets to achieve specific metabolic objectives (Papin, J. A., Reed, J. L. & Palsson, B. O. Hierarchical thinking in network biology: the unbiased modularization of biochemical networks. *Trends Biochem Sci* 29, 641-7 (2004)).

Depending upon the particular environmental conditions being tested and the desired activity, a reaction network data structure can contain smaller numbers of reactions such as at least 200, 150, 100 or 50 reactions. A reaction network data structure having relatively few reactions can provide the advantage of reducing computation time and resources required to perform a simulation. When desired, a reaction network data structure having a particular subset of reactions can be made or used in which reactions that are not relevant to the particular simulation are omitted. Alternatively, larger numbers of reactions can be included in order to increase the accuracy or molecular detail of the methods of the invention or to suit a particular application. Thus, a reaction network data structure can contain at least 300, 350, 400, 450, 500, 550, 600 or more reactions up to the number of reactions that occur in a particular human cell or that are desired to simulate the activity of the full set of reactions occurring in the particular human cell.

A reaction network data structure or index of reactions used in the data structure such as that available in a metabolic reaction database, as described herein, can be annotated to include information about a particular reaction. A reaction can be annotated to indicate, for example, assignment of the reaction to a protein, macromolecule or enzyme that performs the reaction, assignment of a gene(s) that codes for the protein, macromolecule or enzyme, the Enzyme Commission (EC) number of the particular metabolic reaction or Gene Ontology (GO) number of the particular metabolic reaction, a subset of reactions to which the reaction belongs, citations to references from which information was obtained, or a level of confidence with which a reaction is believed to occur in a particular human cell. A computer readable medium of the invention can include a gene database containing annotated reactions. Such information can be obtained during the course of building a metabolic reaction database or model of the invention as described below.

As used herein, the term "gene database" is intended to mean a computer readable medium or media that contains at least one reaction that is annotated to assign a reaction to one or more macromolecules that perform the reaction or to assign one or more nucleic acid that encodes the one or more macromolecules that perform the reaction. A gene database can contain a plurality of reactions, some or all of which are annotated. An annotation can include, for example, a name for a macromolecule; assignment of a function to a macromolecule; assignment of an organism that contains the macromolecule or produces the macromolecule; assignment of a subcellular location for the macromolecule; assignment of conditions under which a macromolecule is regulated with respect to performing a reaction, being expressed or being degraded; assignment of a cellular component that regulates a macromolecule; an amino acid or nucleotide sequence for the macromolecule; or any other annotation found for a macromolecule in a genome database such as those that can be found in Genbank, a site maintained by the NCBI (ncbi.nlm.gov), the Kyoto Encyclopedia of Genes and Genomes (KEGG) (genome.ad.jp/kegg/), the protein database SWISS-PROT (ca.expasy.org/sprot/), the LocusLink database maintained by the NCBI (ncbi.nlm.nih.gov/~ocus~ink/), the Enzyme Nomenclature database maintained by G. P. Moss of Queen Mary and Westfield College in the United Kingdom (chem.qmw.ac.uk/iubmb/enzyme/).

A gene database of the invention can include a substantially complete collection of human genes and/or open reading frames or a substantially complete collection of the macromolecules encoded by the human genome. Alternatively, a gene database can include a portion of human genes or open reading frames or a portion of the macromolecules encoded by the human genome. The portion can be at least 10%, 15%, 20%, 25%, 50%, 75%, 90% or 95% of the human genes or open reading frames encoded by the human genome, or the macromolecules encoded therein. A gene database can also include macromolecules encoded by at least a portion of the nucleotide sequence for the human genome such as at least 10%, 15%, 20%, 25%, 50%, 75%, 90% or 95% of the human genome. Accordingly, a computer readable medium of the invention can include at least one reaction for each macromolecule encoded by a portion of the human genome.

An in silico human metabolic model according to the invention can be built by an iterative process which includes gathering information regarding particular reactions to be added to a model, representing the reactions in a reaction network data structure, and performing preliminary simulations wherein a set of constraints is placed on the reaction network and the output evaluated to identify errors in the network. Errors in the network such as gaps that lead to non-natural accumulation or consumption of a particular metabolite can be identified as described below and simulations repeated until a desired performance of the model is attained.

Thus, the invention provides a method for making or expanding a data structure relating a plurality of *H. sapiens* reactants to a plurality of *H. sapiens* reactions in a computer readable medium. The method includes the steps of: (a) identifying a plurality of *H. sapiens* reactions and a plurality of *H. sapiens* reactants that are substrates and products of the *H. sapiens* reactions; (b) relating the plurality of *H. sapiens* reactants to the plurality of *H. sapiens* reactions in a data structure, wherein each of the *H. sapiens* reactions includes one or more reactants identified as a substrate of the reaction, one or more reactants identified as a product of the reaction and a stoichiometric coefficient relating the substrate and the product; (c) making a constraint set for the plurality of *H. sapiens* reactions; (d) providing an objective function; (e) determining at least one flux distribution that minimizes or maximizes the objective function when the constraint set is applied to the data structure, and (f) if at least one flux distribution is not predictive of human physiology, then adding a reaction to or deleting a reaction from the data structure and repeating step (e), if at least one flux distribution is predictive of human physiology, then storing the data structure in a computer readable medium.

In the course of developing an in silico model of human metabolism, the types of data that can be considered include, for example, biochemical information which is information related to the experimental characterization of a chemical reaction, often directly indicating a protein(s) associated with a reaction and the stoichiometry of the reaction or indirectly demonstrating the existence of a reaction occurring within a cellular extract; genetic information which is information related to the experimental identification and genetic characterization of a gene(s) shown to code for a particular protein(s) implicated in carrying out a biochemical event; genomic information which is information related to the identification of an open reading frame and functional assignment, through computational sequence analysis, that is then linked to a protein performing a biochemical event; physiological information which is information related to overall cellular physiology, fitness characteristics, substrate utilization, and phenotyping results, which provide evidence of the assimilation or dissimilation of a compound used to infer the presence of specific biochemical event (in particular translocations); and modeling information which is information generated through the course of simulating human cellular activity using methods such as those described herein which lead to predictions regarding the status of a reaction such as whether or not the reaction is required to fulfill certain demands placed on a metabolic network. Additional information relevant to multicellular organisms that can be considered includes cell type-specific or condition-specific gene expression information, which can be determined experimentally, such as by gene array analysis or from expressed sequence tag (EST) analysis, or obtained from the biochemical and physiological literature.

The majority of the reactions occurring in human reaction networks are catalyzed by enzymes/proteins, which are created through the transcription and translation of the genes found on the chromosome(s) in the cell. The remaining reactions occur through non-enzymatic processes. Furthermore, a reaction network data structure can contain reactions that add or delete steps to or from a particular reaction pathway. For example, reactions can be added to optimize or improve performance of a *H. sapiens* model in view of empirically observed activity. Alternatively, reactions can be deleted to remove intermediate steps in a pathway when the intermediate steps are not necessary to model flux through the pathway. For example, if a pathway contains three nonbranched steps, the reactions can be combined or added together to give a net reaction, thereby reducing memory required to store the reaction network data structure and the computational resources required for manipulation of the data structure.

The reactions that occur due to the activity of gene-encoded enzymes can be obtained from a genome database which lists genes identified from genome sequencing and subsequent genome annotation. Genome annotation consists of the locations of open reading frames and assignment of function from homology to other known genes or empirically determined activity. Such a genome database can be acquired through public or private databases containing annotated *H. sapiens* nucleic acid or protein sequences. If desired, a model developer can perform a network reconstruction and establish the model content associations between the genes, proteins, and reactions as described, for example, in Covert et al. *Trends in Biochemical Sciences* 26:179-186 (2001) and Palsson, WO 00/46405, incorporated herein by reference.

As reactions are added to a reaction network data structure or metabolic reaction database, those having known or putative associations to the proteins/enzymes which enable/catalyze the reaction and the associated genes that code for these proteins can be identified by annotation. Accordingly, the appropriate associations for some or all of the reactions to their related proteins or genes or both can be assigned. These associations can be used to capture the non-linear relationship between the genes and proteins as well as between proteins and reactions. In some cases, one gene codes for one protein which then performs one reaction. However, often there are multiple genes which are required to create an active enzyme complex and often there are multiple reactions that can be carried out by one protein or multiple proteins that can carry out the same reaction. These associations capture the logic (i.e., AND or OR relationships) within the associations. Annotating a metabolic reaction database with these associations can allow the methods to be used to determine the effects of adding or eliminating a particular reaction not only at the reaction level, but at the genetic or protein level in the context of running a simulation or predicting *Homo sapiens* activity.

The reaction network data structure of the invention can be used to determine the activity of one or more reactions in a plurality of *H. sapiens* reactions independent of any knowledge or annotation of the identity of the protein that performs the reaction or the gene encoding the protein. A model that is annotated with gene or protein identities can include reactions for which a protein or encoding gene is not assigned. While a large portion of the reactions in a cellular metabolic network are associated with genes in the organism's genome, there are also a substantial number of reactions included in a model for which there are no known genetic associations. Such reactions can be added to a reaction database based upon other information that is not necessarily related to genetics such as biochemical or cell based measurements or theoretical considerations based on observed biochemical or cellular activity. For example, there are many reactions that are not protein-enabled reactions. Furthermore, the occurrence of a particular reaction in a cell for which no associated proteins or genetics have been currently identified can be indicated during the course of model building by the iterative model building methods of the invention.

The reactions in a reaction network data structure or reaction database can be assigned to subsystems by annotation, if desired. The reactions can be subdivided according to biological criteria, such as according to traditionally identified metabolic pathways (glycolysis, amino acid metabolism and the like) or according to mathematical or computational criteria that facilitate manipulation of a model that incorporates or manipulates the reactions. Methods and criteria for subdividing a reaction database are described in further detail in Schilling et al., *J. Theor. Biol.* 203:249-283 (2000). The use of subsystems can be advantageous for a number of analysis methods, such as extreme pathway analysis, and can make the management of model content easier. Although assigning reactions to subsystems can be achieved without affecting the use of the entire model for simulation, assigning reactions to subsystems can allow a user to search for reactions in a particular subsystem, which may be useful in performing various types of analyses. Therefore, a reaction network data structure can include any number of desired subsystems including, for example, 2 or more subsystems, 5 or more subsystems, 10 or more subsystems, 25 or more subsystems or 50 or more subsystems.

The reactions in a reaction network data structure or metabolic reaction database can be annotated with a value indicating the confidence with which the reaction is believed to occur in human cells. The level of confidence can be, for example, a function of the amount and form of supporting data that is available. This data can come in various forms including published literature, documented experimental results, or results of computational analyses. Furthermore, the data can provide direct or indirect evidence for the existence of a chemical reaction in a cell based on genetic, biochemical, and/or physiological data.

The invention further provides a computer readable medium, containing (a) a data structure relating a plurality of *H. sapiens* reactants to a plurality of *H. sapiens* reactions, wherein each of the *H. sapiens* reactions includes one or more reactants identified as a substrate of the reaction, one or more reactants identified as a product of the reaction and a stoichiometric coefficient relating the substrate and the product, and (b) a constraint set for the plurality of *H. sapiens* reactions.

Constraints can be placed on the value of any of the fluxes in the metabolic network using a constraint set. These constraints can be representative of a minimum or maximum allowable flux through a given reaction, possibly resulting from a limited amount of an enzyme present. Additionally, the constraints can determine the direction or reversibility of any of the reactions or transport fluxes in the reaction network data structure. Based on the in vivo environment where *H. sapiens* lives the metabolic resources available to the cell for biosynthesis of essential molecules for can be determined. Allowing the corresponding transport fluxes to be active provides the in silico *H. sapiens* with inputs and outputs for substrates and by-products produced by the metabolic network.

The ability of a reaction to be actively occurring is dependent on a large number of additional factors beyond just the availability of substrates. These factors, which can be represented as variable constraints in the models and methods of the invention include, for example, the presence of cofactors necessary to stabilize the protein/enzyme, the presence or absence of enzymatic inhibition and activation factors, the active formation of the protein/enzyme through translation of the corresponding mRNA transcript, the transcription of the associated gene(s) or the presence of chemical signals and/or proteins that assist in controlling these processes that ultimately determine whether a chemical reaction is capable of being carried out within an organism. Of particular importance in the regulation of human cell types is the implementation of paracrine and endocrine signaling pathways to control cellular activities. In these cases a cell secretes signaling molecules that may be carried far afield to act on distant targets (endocrine signaling), or act as local mediators (paracrine signaling). Examples of endocrine signaling molecules include hormones such as insulin, while examples of paracrine signaling molecules include neurotransmitters such as acetylcholine. These molecules induce cellular responses through signaling cascades that affect the activity of biochemical reactions in the cell. Regulation can be represented in an in silico *H. sapiens* model by providing a variable constraint.

The in silico *H. sapiens* model (i.e., Recon 1) and methods described herein can be implemented on any conventional host computer system, such as those based on Intel® or AMD® microprocessors and running Microsoft Windows operating systems. Other systems, such as those using the UNIX or LINUX operating system and based on IBM®, DEC® or Motorola® microprocessors are also contemplated. The systems and methods described herein can also be implemented to run on client-server systems and wide-area networks, such as the Internet.

Software to implement a method or model of the invention can be written in any well-known computer language, such as Java, C, C++, Visual Basic, FORTRAN or COBOL and compiled using any well-known compatible compiler. The software of the invention normally runs from instructions stored in a memory on a host computer system. A memory or computer readable medium can be a hard disk, floppy disc, compact disc, DVD, magneto-optical disc, Random Access Memory, Read Only Memory or Flash Memory. The memory or computer readable medium used in the invention can be contained within a single computer or distributed in a network. A network can be any of a number of conventional network systems known in the art such as a local area network (LAN) or a wide area network (WAN). Client-server environments, database servers and networks that can be used in the invention are well known in the art. For example, the database server can run on an operating system such as UNIX, running a relational database management system, a World Wide Web application and a World Wide Web server. Other types of memories and computer readable media are also contemplated to function within the scope of the invention.

A database or data structure of the invention can be represented in a markup language format including, for example, Standard Generalized Markup Language (SGML), Hypertext markup language (HTML) or Extensible Markup language (XML). Markup languages can be used to tag the information stored in a database or data structure of the invention, thereby providing convenient annotation and transfer of data between databases and data structures. In particular, an XML format can be useful for structuring the data representation of reactions, reactants and their annotations; for exchanging database contents, for example, over a network or internet; for updating individual elements using the document object model; or for providing differential access to multiple users for different information content of a data base or data structure of the invention. XML programming methods and editors for writing XML code are known in the art as described, for example, in Ray, *Learning XML* O'Reilly and Associates, Sebastopol, Calif. (2001).

A computer system of the invention can further include a user interface capable of receiving a representation of one or more reactions. A user interface of the invention can also be capable of sending at least one command for modifying the data structure, the constraint set or the commands for applying the constraint set to the data representation, or a combination thereof. The interface can be a graphic user interface having graphical means for making selections such as menus or dialog boxes. The interface can be arranged with layered screens accessible by making selections from a main screen. The user interface can provide access to other databases useful in the invention such as a metabolic reaction database or links to other databases having information relevant to the reactions or reactants in the reaction network data structure or to human physiology. Also, the user interface can display a graphical representation of a reaction network or the results of a simulation using a model of the invention.

Once an initial reaction network data structure and set of constraints has been created, this model can be tested by preliminary simulation. During preliminary simulation, gaps in the network or "dead-ends" in which a metabolite can be produced but not consumed or where a metabolite can be consumed but not produced can be identified. Based on the results of preliminary simulations areas of the metabolic reconstruction that require an additional reaction can be identified. The determination of these gaps can be readily calculated through appropriate queries of the reaction network data structure and need not require the use of simulation strategies, however, simulation would be an alternative approach to locating such gaps.

In the preliminary simulation testing and model content refinement stage the existing model is subjected to a series of functional tests to determine if it can perform basic requirements such as the ability to produce the required biomass constituents and generate predictions concerning the basic physiological characteristics of the particular organism strain being modeled. The more preliminary testing that is conducted the higher the quality of the model that will be generated. Typically the majority of the simulations used in this stage of development will be single optimizations. A single optimization can be used to calculate a single flux distribution demonstrating how metabolic resources are routed determined from the solution to one optimization problem. An optimization problem can be solved using linear programming as demonstrated in the Examples below. The result can be viewed as a display of a flux distribution on a reaction map. Temporary reactions can be added to the network to determine if they should be included into the model based on modeling/simulation requirements.

Once a model of the invention is sufficiently complete with respect to the content of the reaction network data structure according to the criteria set forth above, the model can be used to simulate activity of one or more reactions in a reaction network. The results of a simulation can be displayed in a variety of formats including, for example, a table, graph, reaction network, flux distribution map or a phenotypic phase plane graph.

Thus, the invention provides a method for predicting a human physiological function. The method includes the steps of (a) providing a data structure relating a plurality of *H. sapiens* reactants to a plurality of *H. sapiens* reactions, wherein each of the *H. sapiens* reactions includes one or more reactants identified as a substrate of the reaction, one or more reactants identified as a product of the reaction and a stoichiometric coefficient relating the substrate and the product; (b) providing a constraint set for the plurality of *H. sapiens* reactions; (c) providing an objective function, and (d) determining at least one flux distribution that minimizes or maximizes the objective function when the constraint set is applied to the data structure, thereby predicting a *H. sapiens* physiological function.

As used herein, the term "physiological function," when used in reference to *H. sapien*, is intended to mean an activity of a human cell as a whole. An activity included in the term can be the magnitude or rate of a change from an initial state of a human cell to a final state of the human cell. An activity can be measured qualitatively or quantitatively. An activity included in the term can be, for example, growth, energy production, redox equivalent production, biomass production, development, or consumption of carbon, nitrogen, sulfur, phosphate, hydrogen or oxygen. An activity can also be an output of a particular reaction that is determined or predicted in the context of substantially all of the reactions that affect the particular reaction in a human cell or substantially all of the reactions that occur in a human cell. Examples of a particular reaction included in the term are production of biomass precursors, production of a protein, production of an amino acid, production of a purine, production of a pyrimidine, production of a lipid, production of a fatty acid, production of a cofactor, production of a hormone, production of a bioactive small molecule, or transport of a metabolite. A physiological function can include an emergent property which emerges from the whole but not from the sum of parts where the parts are observed in isolation (see for example, Palsson *Nat. Biotech* 18:1147-1150 (2000)).

A physiological function of *H. sapiens* reactions can be determined using phase plane analysis of flux distributions. Phase planes are representations of the feasible set which can be presented in two or three dimensions. As an example, two parameters that describe the growth conditions such as substrate and oxygen uptake rates can be defined as two axes of a two-dimensional space. The optimal flux distribution can be calculated from a reaction network data structure and a set of constraints as set forth above for all points in this plane by repeatedly solving the linear programming problem while adjusting the exchange fluxes defining the two-dimensional space. A finite number of qualitatively different metabolic pathway utilization patterns can be identified in such a plane, and lines can be drawn to demarcate these regions. The demarcations defining the regions can be determined using shadow prices of linear optimization as described, for example in Chvatal, *Linear Programming* New York, W.H. Freeman and Co. (1983). The regions are referred to as regions of constant shadow price structure. The shadow prices define the intrinsic value of each reactant toward the objective function as a number that is either negative, zero, or positive and are graphed according to the uptake rates represented by the x and y axes. When the shadow prices become zero as the value of the uptake rates are changed there is a qualitative shift in the optimal reaction network.

One demarcation line in the phenotype phase plane is defined as the line of optimality (LO). This line represents the optimal relation between respective metabolic fluxes. The LO can be identified by varying the x-axis flux and calculating the optimal y-axis flux with the objective function defined as the growth flux. From the phenotype phase plane analysis the conditions under which a desired activity is optimal can be determined. The maximal uptake rates lead to the definition of a finite area of the plot that is the predicted outcome of a reaction network within the environmental conditions represented by the constraint set. Similar analyses can be performed in multiple dimensions where each dimension on the plot corresponds to a different uptake rate. These and other methods for using phase plane analysis, such as those described in Edwards et al., *Biotech Bioeng.* 77:27-36 (2002), can be used to analyze the results of a simulation using an in silico *Homo sapiens* model of the invention.

A physiological function of *H. sapiens* reactions can also be determined using a reaction map to display a flux distribution. A reaction map can be used to view reaction networks at a variety of levels. In the case of a cellular metabolic reaction network, a reaction map can contain the entire reaction complement representing a global perspective. Alternatively, a reaction map can focus on a particular region of metabolism such as a region corresponding to a reaction subsystem described above or even on an individual pathway or reaction.

The invention also provides an apparatus that produces a representation of a *H. sapiens* physiological function, wherein the representation is produced by a process including the steps of: (a) providing a data structure relating a plurality of *H. sapiens* reactants to a plurality of *H. sapiens* reactions, wherein each of the *H. sapiens* reactions includes one or more reactants identified as a substrate of the reaction, one or more reactants identified as a product of the reaction and a stoichiometric coefficient relating the substrate and the product; (b) providing a constraint set for the plurality of *H. sapiens* reactions; (c) providing an objective function; (d) determining at least one flux distribution that minimizes or maximizes the objective function when the constraint set is applied to the data structure, thereby predicting a *H. sapiens* physiological function, and (e) producing a representation of the activity of the one or more *H. sapiens* reactions.

The methods of the invention can be used to determine the activity of a plurality of *H. sapiens* reactions including, for example, biosynthesis of an amino acid, degradation of an amino acid, biosynthesis of a purine, biosynthesis of a pyrimidine, biosynthesis of a lipid, metabolism of a fatty acid, biosynthesis of a cofactor, production of a hormone, production of a bioactive small molecule, transport of a metabolite and metabolism of an alternative carbon source.

The methods of the invention can be used to determine a phenotype of a *H. sapiens* mutant. The activity of one or more *H. sapiens* reactions can be determined using the methods described above, wherein the reaction network data structure lacks one or more gene-associated reactions that occur in *H. sapiens*. Alternatively, the methods can be used to determine the activity of one or more *H. sapiens* reactions when a reaction that does not naturally occur in *H. sapiens* is added to the reaction network data structure. Deletion of a gene can also be represented in a model of the invention by constraining the flux through the reaction to zero, thereby allowing the reaction to remain within the data structure. Thus, simulations can be made to predict the effects of adding or removing genes to or from *H. sapiens*. The methods can be particularly useful for determining the effects of adding or deleting a gene that encodes for a gene product that performs a reaction in a peripheral metabolic pathway.

A drug target or target for any other agent that affects human cellular function can be predicted using the methods of the invention. Such predictions can be made by removing a reaction to simulate total inhibition or prevention by a drug or agent. Alternatively, partial inhibition or reduction in the activity a particular reaction can be predicted by performing the methods with altered constraints. The methods can be particularly useful for identifying a target in a peripheral metabolic pathway.

Once a reaction has been identified for which activation or inhibition produces a desired effect on *H. sapiens* function, an enzyme or macromolecule that performs the reaction in *H. sapiens* or a gene that expresses the enzyme or macromolecule can be identified as a target for a drug or other agent. A candidate compound for a target identified by the methods of the invention can be isolated or synthesized using known methods. Such methods for isolating or synthesizing compounds can include, for example, rational design based on known properties of the target (see, for example, Decamp et al., *Protein Engineering Principles and Practice*, Ed. Cleland and Craik, Wiley-Liss, New York, pp. 467-506 (1996)), screening the target against combinatorial libraries of compounds (see for example, Houghten et al., *Nature*, 354, 84-'86 (1991); Dooley et al., *Science,* 266, 2019-2022 (1994), which describe an iterative approach, or R. Houghten et al. PCT/US91/08694 and U.S. Pat. No. 5,556,762 which describe the positional scanning approach), or a combination of both to obtain focused libraries. Those skilled in the art will know or will be able to routinely determine assay conditions to be used in a screen based on properties of the target or activity assays known in the art.

A candidate drug or agent, whether identified by the methods described above or by other methods known in the art, can be validated using an in silico human metabolic model or method of the invention. The effect of a candidate drug or agent on human physiological function can be predicted based on the activity for a target in the presence of the candidate drug or agent measured in vitro or in vivo. This activity can be represented in an in silico human metabolic model by adding a reaction to the model, removing a reaction from the model or adjusting a constraint for a reaction in the model to reflect the measured effect of the candidate drug or agent on the activity of the reaction. By running a simulation under these conditions the holistic effect of the candidate drug or agent on human physiological function can be predicted.

The methods of the invention can be used to determine the effects of one or more environmental components or conditions on an activity of a *H. sapiens* cell. As set forth above an exchange reaction can be added to a reaction network data structure corresponding to uptake of an environmental component, release of a component to the environment, or other environmental demand. The effect of the environmental component or condition can be further investigated by running simulations with adjusted values for the metabolic flux vector of the exchange reaction target reaction to reflect a finite maximum or minimum flux value corresponding to the effect of the environmental component or condition. The environmental component can be, for example an alternative carbon source or a metabolite that when added to the environment of a *H. sapiens* cell can be taken up and metabolized. The environmental component can also be a combination of components present for example in a minimal medium composition. Thus, the methods can be used to determine an optimal or minimal medium composition that is capable of supporting a particular activity of *H. sapiens*.

The invention further provides a method for determining a set of environmental components to achieve a desired activity for *H. sapiens*. The method includes the steps of providing a data structure relating a plurality of *H. sapiens* reactants to a plurality of *H. sapiens* reactions, wherein each of the *H. sapiens* reactions includes one or more reactants identified as a substrate of the reaction, one or more reactants identified as a product of the reaction and a stoichiometric coefficient relating the substrate and the product; providing a constraint set for the plurality of *H. sapiens* reactions; applying the constraint set to the data representation, thereby determining the activity of one or more *H. sapiens* reactions; determining the activity of one or more *Homo sapiens* reactions according to steps (a) through (c), wherein the constraint set includes an upper or lower bound on the amount of an environmental component, and repeating steps (a) through (c) with a changed constraint set, wherein the activity determined.

Accordingly, reconstruction of the general human metabolic network in a standardized, quality-controlled, bottom-up manner is presented herein. Recon 1 represents a BiGG database that can be mathematically represented and used for in silico study of network properties. This reconstruction can be used to 1) determine gaps in our knowledge base of human metabolism and directly suggest how to fill them, 2) study the systemic and global properties of human metabolism, and 3) provide a context to integrate multiple '-omics' data sets. As with the genome-sequence, the establishment of this map will be an iterative process and Recon 1 is the first comprehensive step towards full delineation of the human metabolic network. It is expected that this global human metabolic reconstruction will be enable significant advances in systems analysis of human biology, as similar reconstructions have successfully enabled analysis of microbial cells (Reed, J. L., Famili, I., Thiele, I. & Palsson, B. O. Towards multidimensional genome annotation. *Nat Rev Genet* 7, 130-41 (2006)). For example, the developing field of nutrigenomics requires significant data integration and analysis to elucidate the influence of the diet on an organism's transcriptome, proteome, and metabolome (Muller, M. & Kersten, S. Nutrigenomics: goals and strategies. *Nat Rev Genet* 4, 315-22 (2003)), and if these ambitious goals are to be met with any degree of success, they will require top-down datasets in conjunction with quantitative, bottom-up reconstructions such as *Homo sapiens* Recon 1.

The following examples are intended to illustrate but not limit the invention.

Example 1

Reconstruction of the Metabolic Network of *H. sapiens*

This example shows how the metabolic network of *H. sapiens* was reconstructed to produce Recon 1.

Reconstruction procedure—An initial component list was assembled as described in the text. This list was then divided into eight metabolic subsets (amino acids, carbohydrates, energy, glycans, lipids, nucleotides, secondary metabolites/xenobiotics, vitamins and cofactors) for independent curation by a team of researchers. Putative gene assignments were verified based on evidence collected from genome annotation databases, namely EntrezGene (Maglott, D., Ostell, J., Pruitt, K. D. & Tatusova, T. Entrez Gene: gene-centered information at NCBI. *Nucleic Acids Res* 33, D54-8 (2005)) and Gene Cards (Safran, M. et al. GeneCards 2002: towards a complete, object-oriented, human gene compendium. *Bioinformatics* 18, 1542-3 (2002)), and the scientific literature. Genes were not included in the network unless there was experimental data supporting their function (i.e., genes were not included if their functional assignment was based on sequence alone). Substrate and cofactor preferences were identified from the literature and BRENDA (Schomburg, I. et al. BRENDA, the enzyme database: updates and major new developments. *Nucleic Acids Res* 32, D431-3 (2004)).

Metabolite formula and charge were calculated based on their ionization state at pH 7.2, which for simplicity was presumed to be constant across all compartments. Reaction reversibility was determined from thermodynamic data or inferred from legacy data and textbooks. Compartmentalization was determined from protein localization data, sequence targeting signals, and indirect physiological evidence. If this data was unavailable, reactions were modeled as cytosolic. The intermembrane space of double-membrane organelles was also modeled as cytosolic. Gene-transcript-protein-reaction relationships were manually identified from the literature and formulated as Boolean logic statements. Isozymes were defined as distinct proteins which could both catalyze the same substrate- and compartment-specific reaction and could arise from one gene due to alternative splicing or could be encoded by independent genes. Cases in which a reaction was dependent on the presence of more than one gene/protein (e.g., proteins with multiple subunits/chains or complexes composed of multiple enzymes) were classified as protein complexes. Confidence scores were assigned based on biological evidence associated with each reaction. Evidence from classical biochemical or genetic experiments, such as gene cloning and protein characterization, were given the highest confidence score (3). Mid-level scores (2) were assigned to reactions based on physiological data or biochemical and genetic evidence from non-mammalian cell (typically mouse, rat, or rabbit). Reactions with the lowest confidence score (1) were included solely based on in silico modeling because, during the process of model validation, they were deemed mandatory for a particular metabolic function. Transport reactions were entirely reconstructed based on literature reports and biochemistry textbooks.

Example 2

Functional Validation and Gap Analysis

Functional validation and gap analysis—The reconstruction was assembled in SimPheny (Genomatica, San Diego) and the stoichiometric matrix was formulated as previously described. Functional validation was performed using flux balance analysis and allowing recycled cofactor pairs to enter and leave the system as needed (see Tables 6-8). Comprehensive gap analysis of the stoichiometric matrix was performed after each round of functional validation. Every metabolite that was not produced or consumed was re-reviewed manually by returning to the literature to identify possible reactions describing its degradation, production, or transport. A final round of gap analysis was performed upon completion of *H. sapiens* Recon 1 (a description of unresolved gaps is provided in Tables 1-5).

Example 3

Network Analysis

Network analysis—Knowledge landscapes were generated for pathways with 5 or more reactions using Matlab v6.5 (The MathWorks, Inc.). Coupled reaction sets were calculated as described by Burgard et al. (Burgard, A. P., Nikolaev, E. V., Schilling, C. H. & Maranas, C. D. Flux coupling analysis of genome-scale metabolic network reconstructions. *Genome Res* 14, 301-12 (2004)) using Matlab v6.5 (The MathWorks, Inc.) for aerobic glucose uptake conditions. Briefly, for all the fluxes in the network under specified input conditions, if two fluxes respond in the same manner (both increase or both decrease) to a perturbation, then they are said to be coupled. Note that variations in transport constraints may affect the composition of the coupled reaction sets.

Example 4

Singular Value Decomposition

The singular value spectra were computed for *H. sapiens* Recon 1, *Saccharomyces cerevisiae* iND750 (Duarte, N. C., Herrgard, M. J. & Palsson, B. O. Reconstruction and validation of *Saccharomyces cerevisiae* iND750, a fully compartmentalized genome-scale metabolic model. *Genome Res* 14, 1298-309 (2004)), and *Escherichia coli* iJR904 (Reed, J. L., Vo, T. D., Schilling, C. H., & Palsson, B. O. An expanded genome-scale model of *Escherichia coli* K-12 (iJR904 GSM/GPR). *Genome Biology* 4, R54.1-R54.12 (2003)) as the normalized cumulative sum of the singular values using Matlab v6.5 (The MathWorks, Inc.). The human and yeast networks were de-compartmentalized by reassigning all intracellular metabolites to the cytosol. Modes were defined as the largest elements (each >0.25*max column value) of the columns of U (identical to the columns of V), where $U\Sigma V^T = \hat{S}\hat{S}^T$ and $\hat{S}$ is the binary form of S.

Example 5

Topological Analysis of RECON 1

This example shows how topological calculations can be performed on RECON 1.

Basic topological statistics of a metabolic network can be quantified and described. The connectivity of each metabolite can be determined by counting the number of reactions in which it appears. For each metabolite, this count is the number of non-zero elements in the corresponding row of the stoichiometric matrix. The result for RECON 1 is that some metabolites participate in many reactions (i.e., over 100), while the majority of metabolites participate in fewer than ten reactions. The connectivity can also be computed for metabolites in each compartment separately.

The mRNA transcripts that encode metabolic enzymes can be correlated to the metabolites they influence through enzymatic activity. This is done by using the gene-protein-reaction associations in conjunction with the stoichiometric matrix. First, each reaction that is associated with a particular mRNA transcript is located. Then, each metabolite that is correlated with each of those reactions is determined. On average, a metabolite is influenced by, for example, 5 or 6 genes, and each gene influences, for example, 8 or 9 metabolites.

The number of metabolites that only occur in one compartment of the reconstruction can be counted. These are the metabolites that are unique to that compartment. Table 10 shows these numbers for each compartment in the reconstruction.

TABLE 10

The number of metabolites unique to each compartment.

| Compartment | Count |
| --- | --- |
| Cytosol | 298 |
| Extracellular | 10 |
| Golgi | 174 |
| Lysosome | 113 |
| Mitochondria | 68 |
| Nucleus | 5 |
| ER | 70 |
| Peroxisome | 26 |

Example 6

Gene Expression Analysis in the Context of RECON 1

This example shows how gene expression or transcriptomic data can be analyzed with RECON 1.

Obesity is a major health problem worldwide. One publication indicates that 65% of adults are overweight (Flegal, et al., *Prevalence and trends in obesity among US adults, 1999-2000.* Jama, 2002. 288(14): p. 1723-7). Gastric bypass surgery is one avenue for treatment available to some obese patients, with Roux-en-Y gastric bypass being the most commonly performed version in the U.S. (Kim, et al., *Surgical treatment for extreme obesity: evolution of a rapidly growing field.* Nutr. Clin. Pract., 2003. 18(2): p. 109-23).

Recon 1 was used to investigate the metabolic effects of gastric bypass surgery in human skeletal muscle. Published gene expression data from the vastus lateralis muscle of three morbidly obese patients was examined before and approximately one year after gastric bypass (Park, et al., *GRB14, GPD1, and GDF8 as potential network collaborators in weight loss-induced improvements in insulin action in human skeletal muscle.* Physiol Genomics, 2006). The data sets were downloaded from Gene Expression Omnibus (GEO) (GEO ID: GSE5109; [169]) and normalized by dividing signal measurements by the average of all measurements on the chip. The $\log_{10}$ ratio of post/pre-surgery expression signals were then calculated for each patient. Probes were mapped to Entrez Gene and RefSeq mRNA IDs [9] in *H. sapiens* Recon 1 based on database identifiers in the Affymetrix U133A Plus 2.0 annotation file (Liu, et al., *NetAffx: Affymetrix probesets and annotations.* 2003. p. 82-86), resulting in a set of 2,071 candidate metabolic probes. The probe list was then further refined to remove probes whose expression ratio was qualitatively inconsistent across all three patients (i.e., not all up or all down). The remaining 516 probes were matched with their corresponding genes and an additional 24 were removed due to qualitative conflicts at the gene level. The average expression ratio was calculated for each gene and then mapped to the reaction network using Recon 1's gene-transcript-protein-reaction associations.

A general trend of up-regulated anaerobic metabolism and down-regulated oxidative phosphorylation was observed post-surgery, with many genes in glycolysis and the pentose phosphate pathway showing subtle, but consistent overall patterns of expression change (Tables 11 and 12). The observed pattern appears to be consistent with the down-regulation of genes involved in mitochondrial bioenergetics that has been observed in the skeletal muscle of rhesus monkeys subjected to long-term caloric restriction (Kayo, et al., *Influences of aging and caloric restriction on the transcriptional profile of skeletal muscle from rhesus monkeys.* Proc Natl Acad Sci USA, 2001. 98(9): p. 5093-8).

TABLE 11

Expression changes in glycolysis/gluconeogenesis for the gastric bypass study.

| Locus | Expr Ratio | Fold change | Gene | Putative function | Reaction |
|---|---|---|---|---|---|
| 5211 | 0.163217 | 1.456187 | PFKL | phosphofructokinase, liver | PFK |
| 229 | 0.188382 | 1.543057 | ALDOB | aldolase B, fructose-bisphosphate | FBA2, FBA4, FBA, FBA5 |
| 5230 | 0.099133 | 1.256414 | PGK1 | phosphoglycerate kinase 1 | PGK |
| 5223 | 0.125026 | 1.333602 | PGAM1 | phosphoglycerate mutase 1 (brain) | DPGase, DPGM, PGM |
| 2023 | 0.075391 | 1.189573 | ENO1 | enolase 1, (alpha) | ENO |
| 26237 | 0.18623 | 1.535429 | ENO1B | enolase alpha, lung-specific | ENO |
| 5315 | 0.481154 | 3.027987 | PKM2 | pyruvate kinase, muscle | PYK |
| 5105 | 0.567078 | 3.690443 | PCK1 | phosphoenolpyruvate carboxykinase 1 (soluble) | PEPCK |
| 98 | −0.16043 | −1.44689 | ACYP2 | acylphosphatase 2, muscle type | ACYP |

Negative ratios indicate a decrease in expression post-surgery.
Expr ratio - average $\log_{10}$ expression ratio (n = 3),
Reaction - reaction abbreviation in *H. sapiens* Recon 1.

TABLE 12

Expression changes in pentose phosphate pathway for the gastric bypass study.

| Locus | Expr Ratio | Fold change | Gene | Putative function | Reaction |
|---|---|---|---|---|---|
| 2539 | −0.09416 | −1.24211 | G6PD | glucose-6-phosphate dehydrogenase | G6PDH2r |
| 8277 | −0.06275 | −1.15544 | TKTL1 | transketolase-like 1 | TKT2, TKT1 |
| 25796 | −0.19013 | −1.54927 | PGLS | 6-phosphogluconolactonase | PGL |
| 64080 | −0.13661 | −1.36964 | RBKS | ribokinase | DRBK, RBK |

Negative ratios indicate a decrease in expression post-surgery.
Expr ratio - average $\log_{10}$ expression ratio (n = 3),
Reaction - reaction abbreviation in *H. sapiens* Recon 1.

Example 7

Analysis of Human Diseases Using RECON 1

The Gene-protein-reaction relationships defined in RECON 1 have enabled the quantitative analysis and assessment of human diseases. As such, information contained in external databases such as the Online Mendelian Inheritance in Man (OMIM) database, currently supported and maintained by the National Center for Biotechnology Information (NCBI), can be integrated into RECON 1.

The contents of OMIM were downloaded and mapped to RECON 1. The Morbid Map subset of OMIM entries correspond to associated diseases and abnormalities in humans resulting from single genetic mutations, multi-gene mutations, and environmental-genetic interactions. 4286 Morbid Map listings were mapped to 2927 unique MIM identification tags. It was noted that the MIM identification tag to gene locus mapping is not necessarily one to one.

The 1496 transcripts in RECON 1 were mapped to the associated loci corresponding to the 2927 MIM tags using the Entrez gene identification. 240 unique loci were mapped to the 238 unique Morbid Map entries, which were associated with 653 reactions in RECON 1. 14 of these were "non-diseases" in which largely benign deviations from normal lab tests were observed (e.g., fructosuria, histidinemia, etc.), and 17 were classified as "susceptibility" mutations (braced entries) in which an associated susceptibility is observed (e.g., alcoholism susceptibility, asthma, autism, M1 susceptibility, obesity, schizophrenia, hypertension). Thus, 207 unique diseases resulted from the mapping.

A global analysis of the network can be carried out to characterize the effect of the different diseases on the function of the network. Flux Variability Analysis (FVA) is a type of optimization analysis built on FBA with involves maximizing and minimizing every flux in a network in order to characterize the capabilities of the network under a specified set of constraints. Results from FVA can be used for a number of purposes including, for example, characterizing the flux span (i.e., the difference between the maximum and minimum flux) for each reaction, and the ability to calculate the volume of the solution space, as the absolute value of the product of all of the fluxes with non-zero flux spans. The principle of FVA can be expanded to the analysis of disease states in networks. This novel approach to characterize effects of altered fluxes in networks to simulate disease states is termed Flux Deletion Variability Analysis (FDVA). This involves changing the constraints of a particular flux, which may involve a partial or a complete reduction or increase in activity, and then carrying out FVA on the network. The effect of decreasing the associated reaction on the network capabilities can be determined by comparing with the FVA results for the initial (unaltered) network. Since some MIM entries were associated with more than one reaction in RECON 1, changing the FDVA for the Morbid Map entries often result in significant curtailment of function in the network, as exhibited by a smaller solution space. FDVA was carried out using RECON 1 under general, open-constraint conditions. It was observed that different diseases affected the size of the solution space in different ways.

Example 8

Analysis of Single Nucleotide Polymorphisms Using RECON 1

The Gene-protein-reaction relationships defined in RECON 1 have provided for the assessment of genetic variations, such as Single Nucleotide Polymorphisms (SNPs), that have been identified in humans. Thus, information available from dbSNP that has been incorporated into the Entrez SNP database, currently supported and maintained by the National Center for Biotechnology Information (NCBI), were integrated into RECON 1.

Based on the contents of the Entrez SNP database as of March 2007, there were 1477 unique SNPs for 1496 gene loci in RECON 1. These 1477 SNP associated loci mapped to 2282 reactions in Recon 1. It was noted that many of these SNPs will not be causal or deleterious. Analysis of these cases using RECON 1 can assist in the illumination of causal and non-causal relationships for 'silent' and altered phenotypes resulting from the SNPs.

Example 9

Integrated Analysis of Human Diseases in the Context of SNPs

The data integration and analysis approaches discussed in Examples 7 and 8 were combined for an integrated analysis of human diseases in the context of SNPs. It was observed that the synergistic integration of these data resulted in a refined analysis of the genotype-phenotype relationship. While there are generalized case-studies of the genotype-phenotype relationship in the literature, RECON 1 provides a global assessment and mapping of diseases and SNPs together. As such, subsequent analysis can illuminate the characterization of causal relationships between changes in DNA sequences, which result in changes in protein composition that may or may not have functional consequences. Constraint based analysis methods (including but not limited to FBA, FVA, FDVA, sampling, and determination of reaction cosets) can be employed in the analysis of the integrated OMIM/SNP mapping to the network.

In the initial analysis carried out for RECON 1 (based on the downloads of the OMIM and Entrez SNP), there were 1339 unique SNPs identified that mapped to 610 unique MIM entries.

Example 10

Identification of New Drug Targets in Humans Using RECON 1

The Gene-protein-reaction relationships defined in RECON 1 with the set of reactions in Table 1 can be used for the analysis of bioactive drugs and drug targets. Coupled reaction sets can be calculated under varying conditions and can be analyzed with respect to multiple different drugs. Mapping experimentally validated drugs to their corresponding drug target reactions in RECON 1 using the gene-protein-reaction relationships will result in the identification of alternative drug targets. Such mapping can be carried out systematically for all known drugs. For example, the Drug-Bank database (Wishart, et al. Nucleic Acids Res 34: D668-72 (2006)) is publicly available and contains over 800 FDA approved drugs and over 3200 experimental drugs. Integrating the DrugBank database into RECON 1 and thereafter mapping drugs to their corresponding site of action will result in 'drug target reaction co-sets', which provide a new set of alternative, but potentially metabolically equivalent therapeutic drug targets.

Throughout this application various publications have been referenced. The disclosures of these publications in their entireties are hereby incorporated by reference in this application in order to more fully describe the state of the art to which this invention pertains.

Further, Tables 1-8 are attached electronically herewith and uploaded via the Electronic Filing System of the United States Patent and Trademark Office. The entire contents of Tables 1-8 are incorporated by reference, and appear as follows:

(a) Table1_IntrasystemReactions.txt—685 KB
(b) Table2_NetworkGaps.txt—121 KB
(c) Table3_Genes.txt—240 KB
(d) Table4_Metabolites.txt—282 KB
(e) Table5_DemandExchangeReactions.txt—28 KB
(f) Table6__288Simulations.txt—9 KB
(g) Table7_Reactions.txt—241 KB
(h) Table8_Metabolites.txt—168 KB Tables 1 and 3-8 were created on Jul. 17, 2007 and Table 2 was created Oct. 3, 2007. Each of the files was uploaded on Oct. 3, 2007.

Although the invention has been described with reference to the above example, it will be understood that modifications and variations are encompassed within the spirit and scope of the invention. Accordingly, the invention is limited only by the following claims.

What is claimed is:

1. A computer readable storage medium having stored thereon computer-implemented instructions causing a processor to perform the steps of:
    (a) providing a data structure relating a plurality of *Homo sapiens* (*H. sapiens*) reactants to a plurality of *H. sapiens* reactions, wherein each of the *H. sapiens* reactions comprises one or more reactants identified as a substrate of the reaction, one or more reactants identified as a product of the reaction, and a stoichiometric coefficient relating the substrate and the product, wherein at least one of the *H. sapiens* reactions is annotated to indicate an associated gene in Table 4;
    (b) providing a gene database comprising information characterizing the associated gene;
    (c) providing a constraint set for the plurality of *H. sapiens* reactions;
    (d) determining at least one flux distribution that minimizes or maximizes an objective function when the constraint set is applied to the data structure, wherein the at least one flux distribution is predictive of a *H. sapiens* physiological function, wherein the data structure comprises Tables 1, 4, 5, 7 and 8; and
    (e) providing information resulting from steps (a) to (d) to a user.

2. The computer readable medium of claim 1, wherein at least one reactant in the plurality of *H. sapiens* reactants or at least one reaction in the plurality of *H. sapiens* reactions is annotated with an assignment to one or more subsystems or compartments.

3. The computer readable medium of claim 1, wherein the plurality of reactions comprises at least one reaction from a *H. sapiens* metabolic network.

4. The computer readable medium of claim 1, wherein the *H. sapiens* physiological function is selected from the group consisting of growth, energy production, redox equivalent production, biomass production, production of biomass precursors, production of a protein, production of an amino acid, production of a purine, production of a pyrimidine, production of a lipid, production of a fatty acid, production of a cofactor, production of a hormone, production of a bioactive small molecule, production of a cell wall component, transport of a metabolite, consumption of carbon, nitrogen, sulfur, phosphate, hydrogen or oxygen, degradation of a protein, degradation of an amino acid, degradation of a purine, degradation of a pyrimidine, degradation of a lipid, degradation of a fatty acid, degradation of a cofactor, and degradation of a cell wall component.

5. The computer readable medium of claim 1, wherein the data structure comprises a set of linear algebraic equations.

6. The computer readable medium of claim 1, wherein the step of determining at least one flux distribution comprises an optimization problem.

7. The computer readable medium of claim 1, wherein a plurality of the *H. sapiens* reactions is annotated to indicate a plurality of associated genes and wherein the gene database comprises information characterizing the plurality of associated genes.

8. A computer readable storage medium having stored thereon computer-implemented instructions causing a processor to perform the steps of:
   (a) providing a data structure relating a plurality of *H. sapiens* reactants to a plurality of *H. sapiens* reactions, wherein each of the *H. sapiens* reactions comprises one or more reactants identified as a substrate of the reaction, one or more reactants identified as a product of the reaction and a stoichiometric coefficient relating the substrate and the product;
   (b) providing a constraint set for the plurality of *H. sapiens* reactions;
   (c) determining at least one flux distribution that minimizes or maximizes an objective function when the constraint set is applied to the data representation, wherein the at least one flux distribution is predictive of *H. sapiens* cellular growth, wherein the data structure comprises Tables 1, 4, 5, 7 and 8; and
   (d) providing information resulting from steps (a) to (c) to a user.

9. A method for predicting a *H. sapiens* physiological function, wherein the steps of the method are performed on a suitably programmed computer programmed to execute the steps comprising:
   (a) providing a data structure relating a plurality of *H. sapiens* reactants to a plurality of reactions, wherein each of the *H. sapiens* reactions comprises one or more reactants identified as a substrate of the reaction, one or more reactants identified as a product of the reaction and a stoichiometric coefficient relating the substrate and the product;
   (b) providing a constraint set for the plurality of *H. sapiens* reactions;
   (c) providing an objective function;
   (d) determining at least one flux distribution that minimizes or maximizes the objective function when the constraint set is applied to the data structure, thereby predicting a *H. sapiens* physiological function related to the gene, wherein the data structure comprises Tables 1, 4, 5, 7 and 8; and
   (e) displaying the prediction to a user.

10. The method of claim 9, wherein at least one of the *H. sapiens* reactions is annotated to indicate an associated gene.

11. The method of claim 9, wherein the plurality of *H. sapiens* reactions comprises at least one reaction from a *H. sapiens* metabolic network.

12. The method of claim 9, wherein the *H. sapiens* physiological function is selected from the group consisting of growth, energy production, redox equivalent production, biomass production, production of biomass precursors, production of a protein, production of an amino acid, production of a purine, production of a pyrimidine, production of a lipid, production of a fatty acid, production of a cofactor, production of a hormone, production of a bioactive small molecule, production of a cell wall component, transport of a metabolite, consumption of carbon, nitrogen, sulfur, phosphate, hydrogen or oxygen, glycolysis, the TCA cycle, pentose phosphate pathway, respiration, biosynthesis of an amino acid, degradation of an amino acid, biosynthesis of a purine, biosynthesis of a pyrimidine, biosynthesis of a lipid, metabolism of a fatty acid, biosynthesis of a cofactor, metabolism of a cell wall component, transport of a metabolite, and metabolism of a carbon source, nitrogen source, oxygen source, phosphate source, hydrogen source or sulfur source.

13. The method of claim 9, wherein the data structure comprises a set of linear algebraic equations.

14. The method of claim 9, further comprising:
   (e) providing a modified data structure, wherein the modified data structure comprises at least one added reaction, compared to the data structure of part (a); and
   (f) determining at least one flux distribution that minimizes or maximizes the objective function when the constraint set is applied to the modified data structure, thereby predicting a *H. sapiens* physiological function.

15. The method of claim 14, further comprising identifying at least one participant in the at least one added reaction.

16. The method of claim 15, further comprising identifying at least one compound that alters the activity or amount of the at least one participant, thereby identifying a candidate drug or agent that alters a *H. sapiens* physiological function.

17. The method of claim 9, further comprising:
   (e) providing a modified data structure, wherein the modified data structure lacks at least one reaction compared to the data structure of part (a); and
   (f) determining at least one flux distribution that minimizes or maximizes the objective function when the constraint set is applied to the modified data structure, thereby predicting a *H. sapiens* physiological function.

18. The method of claim 17, further comprising identifying at least one participant in the at least one reaction.

19. The method of claim 18, further comprising identifying at least one compound that alters the activity or amount of the at least one participant, thereby identifying a candidate drug or agent that alters a *H. sapiens* physiological function.

20. The method of claim 9, further comprising:
   (e) providing a modified constraint set, wherein the modified constraint set comprises a changed constraint for at least one reaction compared to the constraint for the at least one reaction in the data structure of part (a); and
   (f) determining at least one flux distribution that minimizes or maximizes the objective function when the modified constraint set is applied to the data structure, thereby predicting a *H. sapiens* physiological function.

21. The method of claim 20, further comprising identifying at least one participant in the at least one reaction.

22. The method of claim 21, wherein the identifying at least one participant comprises associating a *H. sapiens* protein with the at least one reaction.

23. The method of claim 22, further comprising identifying at least one gene that encodes the protein.

24. The method of claim 21, further comprising identifying at least one compound that alters the activity or amount of the at least one participant, thereby identifying a candidate drug or agent that alters a *H. sapiens* physiological function.

25. A method for predicting human cellular growth, wherein the steps of the method are performed on a suitably programmed computer programmed to execute the steps comprising:

(a) providing a data structure relating a plurality of *H. sapiens* reactants to a plurality of *H. sapiens* reactions, wherein each of the *H. sapiens* reactions comprises one or more reactants identified as a substrate of the reaction, one or more reactants identified as a product of the reaction and a stoichiometric coefficient relating the substrate and the product;

(b) providing a constraint set for the plurality of *H. sapiens* reactions;

(c) providing an objective function;

(d) determining at least one flux distribution that minimizes or maximizes the objective function when the constraint set is applied to the data structure, thereby predicting human cellular growth, wherein the data structure comprises Tables 1, 4, 5, 7 and 8; and (e) displaying the prediction to a user.

* * * * *